(12) United States Patent
Ghadiali

(10) Patent No.: US 10,408,759 B2
(45) Date of Patent: Sep. 10, 2019

(54) METHODS AND SYSTEMS FOR HIGH RESOLUTION FLUORESCENCE MICROSCOPY OF POLYMERIC DYE-LABELED SAMPLES USING POLARIZED LIGHT

(71) Applicant: Becton, Dickinson and Company, Franklin Lakes, NJ (US)

(72) Inventor: James Ghadiali, San Diego, CA (US)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 127 days.

(21) Appl. No.: 15/534,771

(22) PCT Filed: Apr. 25, 2016

(86) PCT No.: PCT/US2016/029249
§ 371 (c)(1),
(2) Date: Jun. 9, 2017

(87) PCT Pub. No.: WO2016/191004
PCT Pub. Date: Dec. 1, 2016

(65) Prior Publication Data
US 2017/0370847 A1  Dec. 28, 2017

Related U.S. Application Data

(60) Provisional application No. 62/166,397, filed on May 26, 2015.

(51) Int. Cl.
*G01N 21/64* (2006.01)
*G01N 15/14* (2006.01)
(Continued)

(52) U.S. Cl.
CPC ..... *G01N 21/6458* (2013.01); *G01N 15/1436* (2013.01); *G01N 15/1475* (2013.01);
(Continued)

(58) Field of Classification Search
CPC .......... G01N 21/6458; G01N 15/1436; G01N 33/582; G01N 15/1475; G01N 21/6428;
(Continued)

(56) References Cited

U.S. PATENT DOCUMENTS 5,457,536 A   10/1995   Kornfield et al.
5,589,936 A   12/1996   Uchikawa et al.
(Continued)

FOREIGN PATENT DOCUMENTS

CA         2858270 A1    6/2013
WO   WO 2004/001379 A2   12/2003
(Continued)

OTHER PUBLICATIONS

Feng et al., "Water-soluble fluorescent conjugated polymers and their interactions with biomacromolecules for sensitive biosensors," Chem. Soc. Rev., 2010, vol. 39, pp. 2411-2419.
(Continued)

*Primary Examiner* — Lore R Jarrett
(74) *Attorney, Agent, or Firm* — Bret E. Field; Bozicevic, Field & Francis LLP

(57) ABSTRACT

Methods for producing a high resolution image of a sample are provided. In some embodiments, the method includes: detecting first and second sets of spatially-dependent emission signals from a sample labeled with a fluorescent polymeric dye; and producing a high resolution fluorescence image of the sample from the detected first and second sets of spatially-dependent emission signals. In some embodiments, the sample is a cell. Also provided are systems for imaging a sample that include a high resolution light microscope including a light source configured to irradiate a field of view with an excitation light; a photodetector configured to detect an emission signal; and a polarization modulator disposed in the light pathway between the light source and
(Continued)

the photodetector; and a sample labelled with a polymeric dye and disposed in the field of view.

19 Claims, 3 Drawing Sheets

(51) Int. Cl.
*G01N 33/58* (2006.01)
*G01N 15/10* (2006.01)

(52) U.S. Cl.
CPC ..... *G01N 21/6428* (2013.01); *G01N 21/6445* (2013.01); *G01N 33/582* (2013.01); *G01N 2015/1006* (2013.01); *G01N 2015/1447* (2013.01); *G01N 2021/6439* (2013.01); *G01N 2201/0683* (2013.01)

(58) Field of Classification Search
CPC ....... G01N 21/6445; G01N 2201/0683; G01N 2015/1447; G01N 2021/6439; G01N 2015/1006
See application file for complete search history.

(56) References Cited

U.S. PATENT DOCUMENTS

| | | |
|---|---|---|
| 7,144,950 B2 | 12/2006 | Bazan et al. |
| 7,214,489 B2 | 5/2007 | Bazan et al. |
| 7,270,956 B2 | 9/2007 | Bazan et al. |
| 7,629,448 B2 | 12/2009 | Bazan et al. |
| 7,666,594 B2 | 2/2010 | Bazan et al. |
| 7,811,755 B2 | 10/2010 | Bazan et al. |
| 7,897,684 B2 | 3/2011 | Bazan et al. |
| 7,914,984 B2 | 3/2011 | Bazan et al. |
| 8,101,416 B2 | 1/2012 | Bazan et al. |
| 8,110,673 B2 | 2/2012 | Bazan et al. |
| 8,158,444 B2 | 4/2012 | Gaylord et al. |
| 8,227,187 B2 | 7/2012 | Bazan et al. |
| 8,338,532 B2 | 12/2012 | Bazan et al. |
| 8,354,239 B2 | 1/2013 | Gaylord et al. |
| 8,362,193 B2 | 1/2013 | Gaylord et al. |
| 8,455,613 B2 | 6/2013 | Gaylord et al. |
| 8,546,081 B2 | 10/2013 | Bazan et al. |
| 8,575,303 B2 | 11/2013 | Gaylord et al. |
| 8,617,814 B2 | 12/2013 | Bazan et al. |
| 8,669,055 B2 | 3/2014 | Bazan et al. |
| 8,759,444 B2 | 6/2014 | Bazan et al. |
| 8,802,450 B2 | 8/2014 | Gaylord et al. |
| 8,835,113 B2 | 9/2014 | Bazan et al. |
| 8,841,072 B2 | 9/2014 | Bazan et al. |
| 8,969,509 B2 | 3/2015 | Liu et al. |
| 8,993,335 B2 | 3/2015 | Bazan et al. |
| 9,085,799 B2 | 7/2015 | Bazan et al. |
| 9,139,869 B2 | 9/2015 | Gaylord et al. |
| 9,159,465 B2 | 10/2015 | Bazan et al. |
| 9,371,559 B2 | 6/2016 | Bazan et al. |
| 9,383,353 B2 | 7/2016 | Gaylord et al. |
| 9,547,008 B2 | 1/2017 | Gaylord et al. |
| 2004/0142344 A1 | 7/2004 | Bazan et al. |
| 2008/0064042 A1 | 3/2008 | Bazan et al. |
| 2008/0293164 A1* | 11/2008 | Gaylord ............... G01N 33/542 436/536 |
| 2010/0136702 A1 | 6/2010 | Bazan et al. |
| 2011/0256549 A1 | 10/2011 | Gaylord et al. |
| 2012/0018651 A1 | 1/2012 | Hess et al. |
| 2012/0028828 A1 | 2/2012 | Gaylord et al. |
| 2012/0252986 A1 | 10/2012 | Liu et al. |
| 2013/0190193 A1 | 7/2013 | Bazan et al. |
| 2014/0030737 A1* | 1/2014 | Holmes ................. G01N 21/17 435/7.24 |
| 2014/0193892 A1 | 7/2014 | Mohan et al. |
| 2015/0226746 A1 | 8/2015 | Bazan et al. |
| 2016/0266132 A1 | 9/2016 | Gaylord et al. |
| 2016/0341720 A1 | 11/2016 | Bazan et al. |
| 2016/0349267 A1 | 12/2016 | Gaylord et al. |
| 2017/0115298 A1 | 4/2017 | Gaylord et al. |

FOREIGN PATENT DOCUMENTS

| | | |
|---|---|---|
| WO | WO 2004/077014 A2 | 9/2004 |
| WO | WO 2004/092324 A2 | 10/2004 |
| WO | WO 2005/086617 A2 | 9/2005 |
| WO | WO 2006/074471 A2 | 7/2006 |
| WO | WO 2006/074482 A2 | 7/2006 |
| WO | WO 2006/083932 A2 | 8/2006 |
| WO | WO 2008/100344 A2 | 8/2008 |
| WO | WO 2010/151807 A1 | 12/2010 |
| WO | WO 2011/091086 A1 | 7/2011 |

OTHER PUBLICATIONS

Gaylord et al. "Water-Soluble Conjugated Oligomers: Effect of Chain Length and Aggregation on Photoluminescence-Quenching Efficiencies," J. Am. Chem. Soc., 2001, vol. 123, No. 26, pp. 6417-6418.

Hafi et al. "Fluorescence nanoscopy by polarization modulation and polarization angle narrowing," Nat. Methods, vol. 11, pp. 579-584 (2014).

Traina et al., "Design and Synthesis of Monofunctionalized, Water-Soluble Conjugated Polymers for Biosensing and Imaging Applications," J. Am. Chem. Soc., 2011, vol. 133, No. 32, pp. 12600-12607.

* cited by examiner

Polymeric tandem dye

Polymeric tandem dye

METHODS AND SYSTEMS FOR HIGH RESOLUTION FLUORESCENCE MICROSCOPY OF POLYMERIC DYE-LABELED SAMPLES USING POLARIZED LIGHT

CROSS-REFERENCE TO RELATED APPLICATIONS

Pursuant to 35 U.S.C. § 119 (e), this application claims priority to the filing date of U.S. Provisional Patent Application Ser. No. 62/166,397, filed May 26, 2015, the disclosure of which application is incorporated herein by reference.

INTRODUCTION

A conventional optical microscope has a fundamental spatial resolution limit dependent on a wavelength of light used and the numerical aperture of the microscope lens. The highest resolution of a conventional optical microscope corresponds to about a half of a wavelength, which is referred to as a diffraction limit. As such, conventional microscopes have a limitation in resolving fluorophores which are separated by less than the diffraction limit.

Circumventing the light diffraction limit, super resolution microscopy produces images with higher spatial resolution measured in nanometers. Signals may be detected from the sequential fluorescence excitation and depletion of fluorophores that have been distributed throughout a sample.

Among the several super resolution microscopy methods, one approach involves the concept of reversible saturable optically linear fluorescence transitions (RESOLFTs) and encompasses stimulated emission depletion (STED) microscopy and saturated structured-illumination microscopy (SSIM). This approach employs lasers that switch fluorophores between a light emitting "on" state and a dark "off" state. As lasers scan a sample, one laser excites fluorophores meant to aid visualization while another suppresses the fluorescence of fluorophores unnecessary for image resolution.

Another approach to super resolution microscopy is super-resolved single fluorophore microscopy, a class of techniques including stochastic optical reconstruction microscopy (STORM), photoactivated localization microscopy (PALM), and fluorescence photoactivation localization microscopy (FPALM). Single fluorophore microscopy techniques account for the diffraction limit by dispersing many photo-switchable fluorescent molecules in a specimen at least 0.2 micrometers apart. After activating just a few fluorescent molecules at a time, a composite image is built by overlaying images taken during each round of excitation. Recent efforts to advance the field of super resolution microscopy include improving upon current features and resolution capabilities, 3D imaging, and multicolor imaging.

Another approach is super resolution by polarization demodulation (SPoD), where adjacent fluorescent dyes in a sample may be distinguished with high resolution using a polarized excitation light. Only the molecules with the correct orientation compatible with the current polarization of the excitation light will fluoresce. This method is performed by rotating the polarization of a wide-field excitation beam and detecting periodic signals from small molecule dyes that emit with different phases. The range of polarization angles that results in effective excitation of differently oriented molecules can be narrowed by rotating a second wide-field de-exciting stimulated emission beam of a polarization perpendicular to the excitation beam polarization (ExPAN), resulting in improved spatial resolution of overlapping fluorescent molecules. SPoD controls the fluorescence modulation frequency of dyes to match camera frame rate of image capture.

SUMMARY

Methods for producing a high resolution image of a sample are provided. In some embodiments, the method includes: detecting first and second sets of spatially-dependent emission signals from a sample labeled with a fluorescent polymeric dye; and producing a high resolution fluorescence image of the sample from the detected first and second sets of spatially-dependent emission signals. In some cases, the sample is a cell and the method further includes contacting the cell with a polymeric dye conjugate that specifically binds a subcellular target under conditions in which the polymeric dye conjugate is localized to the subcellular target location. Also provided are systems for imaging a sample. In some instances, the system includes a high resolution light microscope including a light source configured to irradiate a sample field of view with an excitation light for a fluorescent polymeric dye; a photodetector configured to detect an emission signal from the sample field of view: and a polarization modulator disposed in the light pathway between the light source and the photodetector; and a sample labelled with a polymeric dye and disposed in the sample field of view.

BRIEF DESCRIPTION OF THE FIGURES

It is understood that the drawings, described below, are for illustration purposes only. The drawings are not intended to limit the scope of the present teachings in any way.

FIG. 2A: Irradiation of a polymeric tandem dye with a linearly polarized light beam to produce a fluorescent signal; and FIG. 2B: polarization of a fluorescent emission from a polymeric tandem dye where the exciting light may be polarized or non-polarized.

DEFINITIONS

Figure 1:
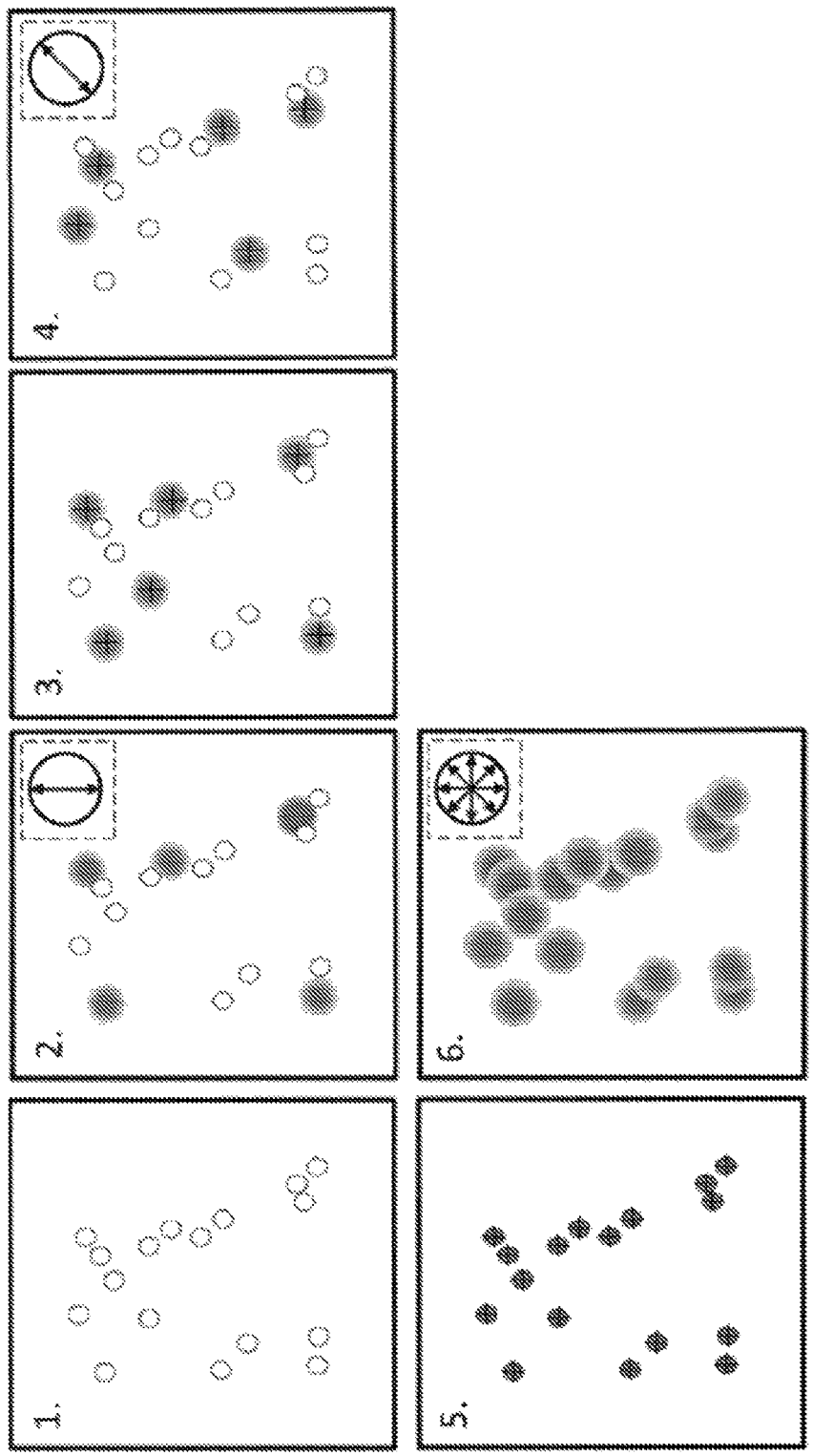
FIG. 1 shows a series of panels illustrating a method of imaging a sample of interest: (Panel 1) Polymeric dyes in a sample assume random orientations; (Panel 2): A subset of the polymeric dyes are excited with plane polarized light and fluorescence is detected. (Panel 3): Coordinates of polymeric dyes are determined with a high accuracy of localization; (Panel 4): The polarization angle is modulated allowing another subset of polymeric dyes of different orientation to become emissive; (Panel 5): Modulation of the polarization angle allows spatial coordinates of all polymeric dyes in the sample to be recorded to high accuracy; and (Panel 6): Imaging with non-polarized light obfuscates the resolution of closely-spaced fluorophores.

Before describing exemplary embodiments in greater detail, the following definitions are set forth to illustrate and define the meaning and scope of the terms used in the description.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

It must be noted that as used herein and in the appended claims, the singular forms "a", "an", and "the" include plural referents unless the context clearly dictates otherwise. For example, the term "a primer" refers to one or more primers, i.e., a single primer and multiple primers. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

A "plurality" contains at least 2 members. In certain cases, a plurality may have 10 or more, such as 100 or more, 1000 or more, 10,000 or more, 100,000 or more, $10^6$ or more, $10^7$ or more, $10^8$ or more or $10^9$ or more members.

Numeric ranges are inclusive of the numbers defining the range.

The term "sample" as used herein relates to a material or mixture of materials, in some cases, although not necessarily, in fluid, i.e., aqueous, form, containing one or more components of interest. Samples may be derived from a variety of sources such as from food stuffs, environmental materials, a biological sample or solid, such as tissue or fluid isolated from an individual, including but not limited to, for example, plasma, serum, spinal fluid, semen, lymph fluid, the external sections of the skin, respiratory, intestinal, and genitourinary tracts, tears, saliva, milk, blood cells, tumors, organs, and also samples of in vitro cell culture constituents (including but not limited to conditioned medium resulting from the growth of cells in cell culture medium, putatively virally infected cells, recombinant cells, and cell components).

Components in a sample are termed "analytes" herein. In many embodiments, the sample is a complex sample containing at least about $10^2$, $5 \times 10^2$, $10^3$, $5 \times 10^3$, $10^4$, $5 \times 10^4$, $10^5$, $5 \times 10^5$, $10^6$, $5 \times 10^6$, $10^7$, $5 \times 10^7$, $10^8$, $10^9$, $10^{10}$, $10^{11}$, $10^{12}$ or more species of analyte.

The term "biological sample" is used in its conventional sense to refer to a whole organism, plant, fungi or a subset of animal tissues, cells or component parts which may in certain instances be found in blood, mucus, lymphatic fluid, synovial fluid, cerebrospinal fluid, saliva, bronchoalveolar lavage, amniotic fluid, amniotic cord blood, urine, vaginal fluid and semen. As such, a "biological sample" refers to both the native organism or a subset of its tissues as well as to a homogenate, lysate or extract prepared from the organism or a subset of its tissues, including but not limited to, for example, plasma, serum, spinal fluid, lymph fluid, sections of the skin, respiratory, gastrointestinal, cardiovascular, and genitourinary tracts, tears, saliva, milk, blood cells, tumors, organs. Biological samples may be any type of organismic tissue, including both healthy and diseased tissue (e.g., cancerous, malignant, necrotic, etc.). In certain embodiments, the biological sample is a liquid sample, such as blood or derivative thereof, e.g., plasma, tears, urine, semen, etc., where in some instances the sample is a blood sample, including whole blood, such as blood obtained from venipuncture or fingerstick (where the blood may or may not be combined with any reagents prior to assay, such as preservatives, anticoagulants, etc.). Biological samples may include cells.

In certain embodiments the source of the sample is a "mammal" or "mammalian", where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In some instances, the subjects are humans. The methods may be applied to samples obtained from human subjects of both genders and at any stage of development (i.e., neonates, infant, juvenile, adolescent, adult), where in certain embodiments the human subject is a juvenile, adolescent or adult. While the present invention may be applied to samples from a human subject, it is to be understood that the methods may also be carried-out on samples from other animal subjects (that is, in "non-human subjects") such as, but not limited to, birds, mice, rats, dogs, cats, livestock and horses.

The term "analyte" refers to a known or unknown component of a sample, which will specifically bind to a capture agent if the analyte and the capture agent are members of a specific binding pair. In general, analytes are biopolymers, i.e., an oligomer or polymer such as an oligonucleotide, a peptide, a polypeptide, an antibody, or the like. In some cases, an "analyte" is referenced as a moiety in a sample, to be detected by a "capture agent" which, in most embodiments, is bound to a polymeric dye, e.g., a polymeric dye conjugate.

As used herein, the terms "capture agent" and "specific binding member" are used interchangeably to refer to a molecule or a multi-molecular complex which can specifically bind an analyte, e.g., specifically bind an analyte for the capture agent with a dissociation constant ($K_D$) of less than about $10^{-6}$ without binding to other targets. The binding interaction is in some cases mediated by an affinity region of the capture agent. Capture agents of interest include antibodies, which are well known in the art. Capture agents usually "specifically bind" one or more analytes.

A "biopolymer" is a polymer of one or more types of repeating units, regardless of the source. Biopolymers may be found in biological systems and particularly include polypeptides and polynucleotides, as well as such compounds containing amino acids, nucleotides, or analogs thereof. The term "polynucleotide" refers to a polymer of nucleotides, or analogs thereof, of any length, including oligonucleotides that range from 2-100, such as 10-100 nucleotides in length and polynucleotides of greater than 100 nucleotides in length. The term "polypeptide" refers to a polymer of amino acids of any length, including peptides that range from 2-50, such as 6-50 amino acids in length and polypeptides that are greater than 50 amino acids in length. In most embodiments, the terms "polypeptide" and "protein" are used interchangeably. The term "polypeptide" includes polypeptides in which the conventional backbone has been replaced with non-naturally occurring or synthetic backbones, and peptides in which one or more of the conventional amino acids have been replaced with a non-naturally occurring or synthetic amino acid capable of participating in peptide bonding interactions. The terms "polypeptide" and "protein", used interchangeably herein, refer to a polymeric form of amino acids of any length, which can include coded and non-coded amino acids, chemically or biochemically modified or derivatized amino acids, and polypeptides having modified peptide backbones.

In general, polypeptides may be of any length, e.g., greater than 2 amino acids, greater than 4 amino acids, greater than about 10 amino acids, greater than about 20 amino acids, greater than about 50 amino acids, greater than about 100 amino acids, greater than about 300 amino acids, usually up to about 500 or 1000 or more amino acids. "Peptides" are generally greater than 2 amino acids, greater than 4 amino acids, greater than about 10 amino acids, greater than about 20 amino acids, usually up to about 50 amino acids. In some embodiments, peptides are between 5 and 30 amino acids in length.

The term "specific binding" refers to the ability of a capture agent to preferentially bind to a particular analyte that is present in a homogeneous mixture of different analytes. In some cases, a specific binding interaction will discriminate between desirable and undesirable analytes in a sample, in some cases more than about 10 to 100-fold or more (e.g., more than about 1000-fold). In some cases, the affinity between a capture agent and analyte when they are specifically bound in a capture agent/analyte complex is at least $10^{-8}$ M, at least $10^{-9}$ M, usually up to about $10^{-10}$ M.

A capture agent and an analyte for the capture agent will in some cases specifically bind to each other under "conditions suitable to for specific binding", where such conditions are those conditions (in terms of salt concentration, pH, detergent, protein concentration, temperature, etc.) which allow for binding to occur between capture agents and analytes to bind in solution. Such condition, particularly with respect to antibodies and their antigens, are well known in the art (see, e.g., Harlow and Lane (Antibodies: A Laboratory Manual Cold Spring Harbor Laboratory, Cold Spring Harbor, N.Y. (1989)). Conditions suitable for specific binding in some cases permit capture agents and target pairs that have a dissociation constant ($K_D$) of less than about $10^{-6}$ to bind to each other, but not with other capture agents or targets.

As used herein, the term "linker" or "linkage" refers to a linking moiety that connects two groups and has a backbone of 20 atoms or less in length. A linker or linkage may be a covalent bond that connects two groups or a chain of between 1 and 20 atoms in length, for example a chain of 1, 2, 3, 4, 5, 6, 8, 10, 12, 14, 16, 18 or 20 carbon atoms in length, where the linker may be linear, branched, cyclic or a single atom. In certain cases, one, two, three, four or five or more carbon atoms of a linker backbone may be optionally substituted with a sulfur, nitrogen or oxygen heteroatom. The bonds between backbone atoms may be saturated or unsaturated, and in some cases not more than one, two, or three unsaturated bonds are present in a linker backbone. The linker may include one or more substituent groups, for example with an alkyl, aryl or alkenyl group. A linker may include, without limitations, polyethylene glycol; ethers, thioethers, tertiary amines, alkyls, which may be straight or branched, e.g., methyl, ethyl, n-propyl, 1-methylethyl (isopropyl), n-butyl, n-pentyl, 1,1-dimethylethyl (t-butyl), and the like. The linker backbone may include a cyclic group, for example, an aryl, a heterocycle or a cycloalkyl group, where 2 or more atoms, e.g., 2, 3 or 4 atoms, of the cyclic group are included in the backbone. A linker may be cleavable or non-cleavable.

As used herein, the term "alkyl" by itself or as part of another substituent refers to a saturated branched or straight-chain monovalent hydrocarbon radical derived by the removal of one hydrogen atom from a single carbon atom of a parent alkane. Alkyl groups of interest include, but are not limited to, methyl; ethyl, propyls such as propan-1-yl or propan-2-yl; and butyls such as butan-1-yl, butan-2-yl, 2-methyl-propan-1-yl or 2-methyl-propan-2-yl. In some embodiments, an alkyl group includes from 1 to 20 carbon atoms. In some embodiments, an alkyl group includes from 1 to 10 carbon atoms. In certain embodiments, an alkyl group includes from 1 to 6 carbon atoms, such as from 1 to 4 carbon atoms.

"Aryl" by itself or as part of another substituent refers to a monovalent aromatic hydrocarbon radical derived by the removal of one hydrogen atom from a single carbon atom of an aromatic ring system. Aryl groups of interest include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In certain embodiments, an aryl group includes from 6 to 20 carbon atoms. In certain embodiments, an aryl group includes from 6 to 12 carbon atoms. Examples of an aryl group are phenyl and naphthyl.

"Heteroaryl" by itself or as part of another substituent, refers to a monovalent heteroaromatic radical derived by the removal of one hydrogen atom from a single atom of a heteroaromatic ring system. Heteroaryl groups of interest include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, triazole, benzotriazole, thiophene, triazole, xanthene, benzodioxole and the like. In certain embodiments, the heteroaryl group is from 5-20 membered heteroaryl. In certain embodiments, the heteroaryl group is from 5-10 membered heteroaryl. In certain embodiments, heteroaryl groups are those derived from thiophene, pyrrole, benzothiophene, benzofuran, indole, pyridine, quinoline, imidazole, oxazole and pyrazine.

"Substituted" refers to a group in which one or more hydrogen atoms are independently replaced with the same or different substituent(s). Substituents of interest include, but are not limited to, alkylenedioxy (such as methylenedioxy), -M, $-R^{60}$, $-O^-$, $=O$, $-OR^{60}$, $-SR^{60}$, $-S^-$, $=S$, $-NR^{60}R^{61}$, $=NR^{60}$, $-CF_3$, $-CN$, $-OCN$, $-SCN$, $-NO$, $-NO_2$, $=N_2$, $-N_3$, $-S(O)_2O^-$, $-S(O)_2OH$, $-S(O)_2R^{60}$, $-OS(O)_2O^-$, $-OS(O)_2R^{60}$, $-P(O)(O^-)_2$, $-P(O)(OR^{60})(O^-)$, $-OP(O)(OR^{60})(OR^{61})$, $-C(O)R^{60}$, $-C(S)R^{60}$, $-C(O)OR^{60}$, $-C(O)NR^{60}R^{61}$, $-C(O)O^-$, $-C(S)OR^{60}$, $-NR^{62}C(O)NR^{60}R^{61}$, $-NR^{62}C(S)NR^{60}R^{61}$, $-NR^{62}C(NR^{63})NR^{60}R^{61}$ and $-C(NR^{62})NR^{60}R^{61}$ where M is halogen; $R^{60}$, $R^{61}$, $R^{62}$ and $R^{63}$ are independently hydrogen, alkyl, substituted alkyl, alkoxy, substituted alkoxy, cycloalkyl, substituted cycloalkyl, cycloheteroalkyl, substituted cycloheteroalkyl, aryl, substituted aryl, heteroaryl or substituted heteroaryl, or optionally $R^{60}$ and $R^{61}$ together with the nitrogen atom to which they are bonded form a cycloheteroalkyl or substituted cycloheteroalkyl ring; and $R^{64}$ and $R^{65}$ are independently hydrogen, alkyl, substituted alkyl, aryl, cycloalkyl, substituted cycloalkyl, cycloheteroalkyl, substituted cycloheteroalkyl, aryl, substituted aryl, heteroaryl or substituted heteroaryl, or optionally $R^{64}$ and $R^{65}$ together with the nitrogen atom to which they are bonded form a cycloheteroalkyl or substituted cycloheteroalkyl ring. In certain embodiments, substituents include -M, —$R^{60}$, =O, $OR^{60}$, —$SR^{60}$, —$S^-$, =S, —$NR^{60}R^{61}$, =$NR^{60}$, —$CF_3$, —CN, —OCN, —SCN, —NO, —$NO_2$, =$N_2$, —$N_3$, —$S(O)_2R^{60}$, $OS(O)_2O$, —$OS(O)_2R^{60}$, —P(O)$(O^-)_2$, —P(O)$(OR^{60})(O^-)$, —OP(O)$(OR^{60})(OR^{61})$, —C(O)$R^{60}$, —C(S)$R^{60}$, —C(O)$OR^{60}$, —C(O)$NR^{60}R^{61}$, —C(O)$O^-$, —$NR^{62}$C(O)$NR^{60}R^{61}$. In certain embodiments, substituents include -M, —$R^{60}$, =O, —$OR^{60}$, —$SR^{60}$, —$NR^{60}R^{61}$, —$CF_3$, —CN, —$NO_2$, —$S(O)_2R^{60}$, —P(O)$(OR^{60})(O^-)$, —OP(O)$(OR^{60})(OR^{61})$, —C(O)$R^{60}$, —C(O)$OR^{60}$, —C(O)$NR^{60}R^{61}$, —C(O)$O^-$. In certain embodiments, substituents include -M, —$R^{60}$, =O, —$OR^{60}$, —$SR^{60}$, —$NR^{60}R^{61}$, —$CF_3$, —CN, —$NO_2$, —$S(O)_2R^{60}$, —OP(O)$(OR^{60})(OR^{61})$, —C(O)$R^{60}$, —C(O)$OR^{60}$, —C(O)$O^-$, where $R^{60}$, $R^{61}$ and $R^{62}$ are as defined above. For example, a substituted group may bear a methylenedioxy substituent or one, two, or three substituents selected from a halogen atom, a (1-4C)alkyl group and a (1-4C)alkoxy group. When the group being substituted is an aryl or heteroaryl group, the substituent(s) (e.g., as described herein) may be referred to as "aryl substituent(s)".

The methods described herein include multiple steps. Each step may be performed after a predetermined amount of time has elapsed between steps, as desired. As such, the time between performing each step may be 1 second or more, 10 seconds or more, 30 seconds or more, 60 seconds or more, 5 minutes or more, 10 minutes or more, 60 minutes or more and including 5 hours or more. In certain embodiments, each subsequent step is performed immediately after completion of the previous step. In other embodiments, a step may be performed after an incubation or waiting time after completion of the previous step, e.g., a few minutes to an overnight waiting time.

Other definitions of terms may appear throughout the specification.

DETAILED DESCRIPTION

As summarized above, methods for producing a high resolution image of a sample are provided. In some embodiments, the method includes: detecting first and second sets of spatially-dependent emission signals from a sample labeled with a fluorescent polymeric dye; and producing a high resolution fluorescence image of the sample from the detected first and second sets of spatially-dependent emission signals. In some cases, the sample is a cell and the method further includes contacting the cell with a polymeric dye conjugate that specifically binds a subcellular target under conditions in which the polymeric dye conjugate is localized to the subcellular target location. Also provided are systems for imaging a sample. In some instances, the system includes a high resolution light microscope including a light source configured to irradiate a sample field of view with an excitation light for a fluorescent polymeric dye; a photodetector configured to detect an emission signal from the sample field of view: and a polarization modulator disposed in the light pathway between the light source and the photodetector; and a sample labelled with a polymeric dye and disposed in the sample field of view.

Before the various embodiments are described in greater detail, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

The citation of any publication is for its disclosure prior to the filing date and should not be construed as an admission that the present claims are not entitled to antedate such publication by virtue of prior invention. Further, the dates of publication provided can be different from the actual publication dates which can be independently confirmed.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

All patents and publications, including all sequences disclosed within such patents and publications, referred to herein are expressly incorporated by reference.

In further describing the subject invention, methods for producing a high resolution image of a sample are described first in greater detail, including high resolution cellular imaging methods. Next, polymeric dyes and conjugates thereof which find use in the subject methods are described. Then, systems that may be used in practicing the subject methods are described.

Methods of Imaging a Polymeric Dye Labeled Sample

As summarized above, the present disclosure provides a method for producing a high resolution image of a sample. In some cases, the method includes high resolution fluorescence microscopy. Fluorescence microscopy uses fluorescence instead of reflection or absorption of light in the imaging of a sample of interest. As such, a sample is irradiated with light of a suitable excitation wavelength that is absorbed by fluorophores of interest, causing the fluorophores to emit light at an emission wavelength. The process can be carried out using wide-field irradiation of the sample or by scanning a fine beam of excitation light over the sample, e.g., using confocal laser scanning microscopy. The wave characteristics of the excitation light limits the size of the spot to which light can be focused due to the diffraction limit. An approximation of the resolution attainable is the full width at half maximum (FWHM) of the point spread function. For example, a wide field microscope with high numerical aperture and visible light in some cases attains a resolution of about 250 nm.

Super-resolution techniques may be used to capture fluorescent images of samples of interest with a higher resolution than the diffraction limit. A variety of microscopy methods may be adapted for use in the subject methods including, but are not limited to, methods for sub diffraction-limited imaging of a sample, such as, polarization-based super resolution microscopy (SPoD), stochastic optical reconstruction microscopy (STORM), photoactivated localization microscopy (PALM), stimulated emission depletion microscopy (STED) and structured illumination microscopy (SIM) optical antennas, near-field scanning optical microscope (NSOM), near-field optical random mapping (NORM) microscopy, spatially modulated illumination (SMI) microscopy, ground state depletion (GSD), saturated structured illumination microscopy (SSIM), SPDM (Spectral Precision Distance Microscopy) and single-molecule localization microscopy (SMLM).

Figure 3:
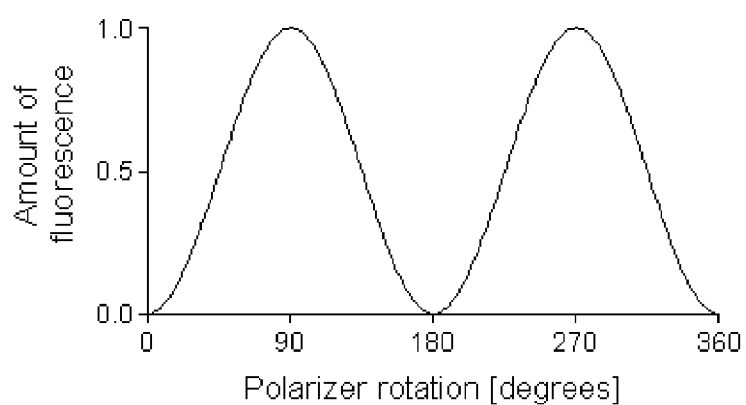
FIG. 3 illustrates the dependence of fluorescence on the rotation of the polarizer in SPoD. The relationship may apply to both linear dichroism and fluorescence polarization configurations depicted in FIG. 2A and FIG. 2B, respectively.

In fluorescence microscopy, when differently orientated fluorescent dyes are excited with linear rotating polarized light, the dyes emit periodic emission signals which peak in intensity at different times (see, e.g., FIG. 3). Effective excitation of an oriented fluorescent dye molecule is dependent on a polarization angle range of the excitation light. In some cases, excitation polarization angle narrowing (ExPAN) may be used to generate short periodic emission flashes and provide discrimination between fluorescent molecules or fluorescent nanoscale areas of a sample. It is understood that both linear dichroism and florescence polarization methods may be utilized with polarized light to yield the information about the orientation of a fluorescent dye.

In contrast to a small molecule dye, a polymeric dye may have a significantly larger and extended linear structure, which in some cases may resemble a rigid-rod like structure. Polymeric dye molecules distributed at particular spatial locations within a sample may independently adopt random orientations of their extended linear structure. By irradiating a sample labeled with polymeric dye with polarized light, a photoselection process takes place, in which only a subset of the polymeric dye molecules whose orientation has an appropriate alignment relative to the direction of polarization will fluoresce. Such polarization-based emission signals of a polymeric dye in a sample may be referred to as being "spatially-dependent" since the fluorescence intensity will depend on the orientations of the polymeric dye molecules at particular spatial locations. Because of their relative size and structure, polymeric dyes may exhibit slow kinetics of molecular motion relative to small molecule fluorophores and have reduced freedom of movement in a sample. As such, a polymeric dye may be effectively excited within a narrow range of light polarization angles. In combination with desirable spectroscopic properties, such as high extinction coefficient and high quantum yield, individual polymeric dyes may be precisely located with high resolution in a sample using the subject methods. The subject methods may also be performed without the need for a second light beam for excitation polarization angle narrowing (ExPAN) that is utilized in SPoD microscopy of small molecule dyes.

The subject methods of fluorescence microscopy include detecting sets of spatially-dependent emission signals from a sample of interest that is labeled with a polymeric dye. As used here, the term "spatially-dependent emission signal" refers to a fluorescence emission signal originating from a polymeric dye in a sample that is dependent on the alignment of the oriented polymeric dye relative to the polarization angle of a light polarizer in the light pathway (e.g., in the excitation light pathway and/or the emission signal pathway as described herein). A "set" of spatially-dependent emission signals refers to a group of spatially-dependent emission signals that originate from a subset of the total polymeric dyes in a sample and which are characterized by all having similar molecular orientations and alignments with the light polarization angle. As used herein, the terms "fluorescence", "emission light" and "emission signal" are used interchangeably to refer to the emission of light from a fluorescent polymeric dye of interest. The emission light may refer to light emitted from individual polymeric dye molecules or to total light emitted from a polymeric dye-labeled sample.

As such, the spatial locations of the first subset of polymeric dye molecules in the sample define a spatial distribution of emission signals that are detected in the sample field of view. These emission signals may fluctuate as a function of the polarization angle, depending on the alignment of the polymeric dye molecule from which a particular emission signal of interest originates. As such, the oriented polymeric dye molecules in the sample may emit a periodic emission signal (e.g., move from an emissive to a non-emissive state as depicted in FIG. 3) in conjunction with changes in the polarization angle. A first set of spatially-dependent emission signals that originates from a first subset of the total polymeric dye molecules in a sample may be detected at a first polarization angle. A second set of spatially-dependent emission signals that originate from a second distinct subset of the total polymeric dye molecules in a sample may be detected at a second polarization angle. A first or second set of polymeric dyes in the sample that is imaged at any one polarization angle may represent 0.5 or less of the total number of polymeric dyes present in the sample, such as 0.4 or less, 0.3 or less, 0.2 or less, 0.1 or less, 0.05 less, 0.01 or less, 0.005 or less, 0.003 or less, 0.001 or less, or even less.

The spatial point origins of these emission signals, and thus the location of a corresponding polymeric dye molecule, may be recorded and integrated to build a high resolution fluorescent image of the sample in the field of view. By detecting such spatially-dependent fluorescence emission signals from only a subset of the polymeric dyes in a sample at a time, the spatial coordinates of all the polymeric dyes in the sample can be integrated with high accuracy and high resolution. Closely spaced polymeric dyes in the sample can be distinguished and separately imaged with high resolution without obfuscation that occurs with non-polarized light imaging, based on their relative alignments.

Methods that include linear dichroism and/or methods that include fluorescence polarization may be adapted for use in the subject methods. In the extended linear structure of a polymeric dye, the transition dipole moments (TDMs) of the optically-active units of the multichromophore which makes up the polymeric dye may be aligned along the long axis of the molecule. The TDM of a molecule refers to the electric dipole moment associated with the transitions between two states of a molecule, e.g., the transition between an excited state and ground state of a fluorophore. A polymeric dye is a light harvesting multichromophore that may absorb incident light having a suitable excitation wavelength, e.g., a wavelength that is close to the absorption maximum wavelength of the polymeric dye. Electromagnetic waves, such as light, exhibit polarization where the waves can oscillate in a variety of different directions. Light polarization refers to the polarization of the electric field component of light where the light waves have vibrations that occur in a single plane. The process of transforming unpolarized light into polarized light is known as polarization. In order for a photon to be absorbed by a molecule through single-photon absorption, the electric field of the light wave has to push the electrons in the molecule in the direction of the transition dipole moment (TDM). If the direction of the electric field vector of the excitation light is parallel to the TDM, the rate of light absorption by the molecule is maximal. If the two vectors (the electric field vector of light and the TDM of the dye) are perpendicular, no light absorption occurs. When a polymeric dye's transition dipole moment is aligned parallel to the electric field vector of incident light of a suitable wavelength (the "excitation light"), the polymeric dye may absorb incoming photons and then subsequently emit light or fluoresce (i.e., an emission signal).

As such, the polymeric dyes which find use in the subject methods may have polarization-dependent fluorescence. In addition, the movement of electrons (charges) along the polymeric dye backbone leads to emission of electromagnetic waves according to the laws of dipole radiation. Light that is emitted from the polymeric dye may also have a particular electric field vector that is dependent on the orientation of the polymeric dye's transition dipole moment, and thus the spatial orientation and alignment of the molecule. Any convenient fluorescence microscopy methods may be may be adapted for use in the subject methods including, but not limited to, fluorescence polarization methods, linear dichroism methods and those polarization-based super resolution microscopy (SPoD) methods described by Walla et al., in "Fluorescence nanoscopy by polarization modulation and polarization angle narrowing", Nature Methods 11, 579-584 (2014) and in CA2858270, as described in greater detail herein.

Figure 2A:
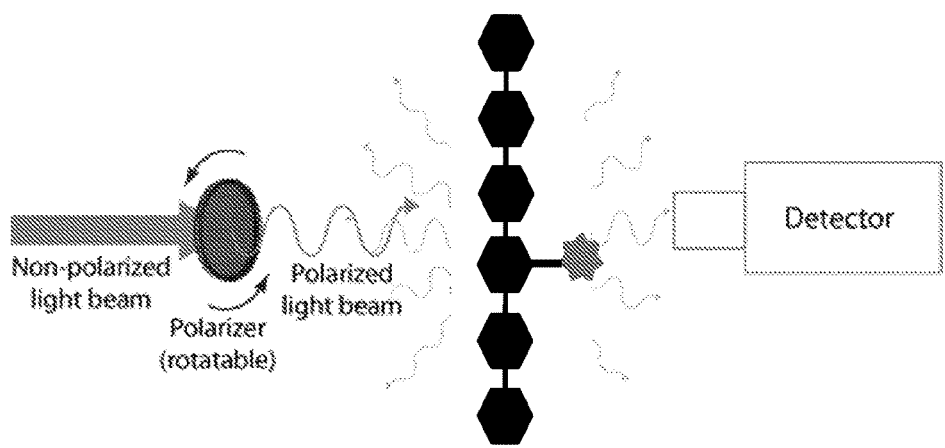
FIGS. 2A-2B depict two configurations of systems that find use in the subject methods.

In some cases, the method includes polarizing an excitation light to produce a fluorescence emission light from a polymeric dye molecule excited by the polarized excitation light. As such, the excitation light may be a polarized excitation light. FIG. 2A illustrates the placement of a polarizer in an excitation light pathway (i.e., the pathway between the light source and the sample field of view) in order to excite an exemplary polymeric dye. In some embodiments of the method, the excitation light is linearly polarized. As described above, the alignment of an oriented polymeric dye molecule relative to a polarizer in the excitation light pathway can determine the extent of absorption of polarized excitation light by the molecule and thus can determine the amount of emission light collected at a detector.

Figure 2B:
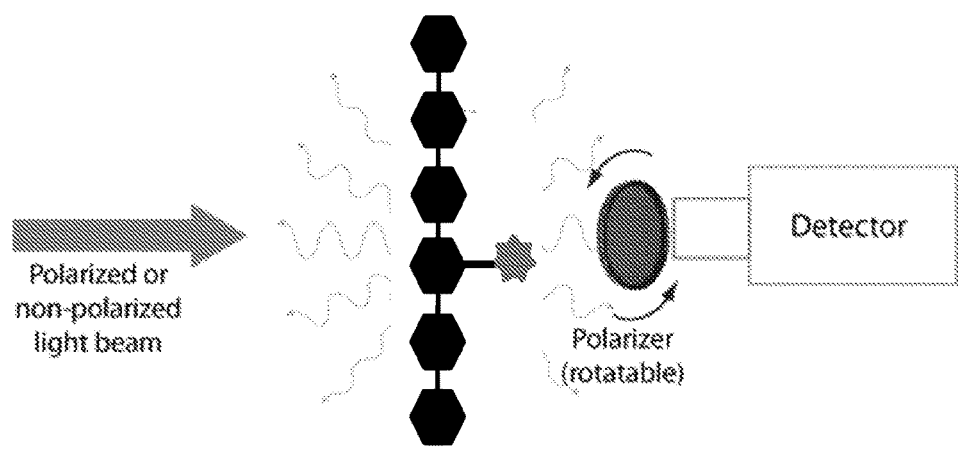

In certain cases, the method includes polarizing a fluorescence emission light from a polymeric dye in the emission pathway between the polymeric dye and the detector using a polarization device. As such the fluorescence emitted by a polymeric dye in the sample may be polarized. In some embodiments of the method, the emission signals are linearly polarized. Polymeric dye molecules in a sample can be excited with a polarized light or a non-polarized light, and the fluorescence from the polymeric dyes can be polarized in the emission pathway (i.e., the pathway between the sample field of view and the detector) prior to collection at the detector. In that way, only polarized light from the subset of polymeric dye molecules having an appropriate orientation relative to the direction of polarization is detected, dependent on the local alignments of the molecules at particular spatial locations in the sample. FIG. 2B illustrates the placement of a polarizer in an emission light pathway in order to generate a polarized fluorescence emission signal from an exemplary polymeric tandem dye. In some instances, the excitation light is unpolarized. In certain instances, a combination of the two polarization strategies may be utilized, where polarization of both the excitation light and the emission light is performed (e.g., FIG. 2B where the excitation light is polarized). As such, the alignment of a polymeric dye molecule relative to a polarizer in the emission light pathway determines the amount (i.e., intensity) of light collected at the detector.

Under either polarization approach (see e.g., FIG. 2A versus 2B), subsequently modulating the polarization angle allows, in turn, a second subset of dye molecules to be detected whereas the previously emissive dyes of the first subset will enter a non-detected state (see e.g., FIG. 1, panels 3 and 4). For example, under a linear dichroism strategy, by modulating the polarization of excitation light across a range of angles, different subsets of dyes will enter emissive and non-emissive states in a periodic manner as a function of polarization angle (see e.g., FIG. 3 which illustrates such a periodic function). In certain embodiments, the method includes modulating the polarization angle of the excitation light from a first polarization angle at which the first set of spatially-dependent emission signals is produced to a second polarization angle at which the second set of spatially-dependent emission signals is produced. The spatial point origins of these detected periodic emissive centers are recorded and integrated to build a high-resolution fluorescent image of the sample. This is in contrast to standard wide field fluorescence microscopy in which all fluorescent molecules within the sample are emissive simultaneously; reducing the ability to resolve closely separated structural features.

In some embodiments of the method, the emission light from the sample is polarized to produce the first and second sets of spatially-dependent emission signals. In certain embodiments, the excitation light is unpolarized, but any emission light from a polymeric dye of interest is polarized prior to detection. In certain embodiments, the method includes irradiating the sample with unpolarized excitation light. As used herein, the terms "unpolarized" and "non-polarized" are used interchangeably. In certain embodiments, where the emission light from the sample is polarized to produce the first and second sets of spatially-dependent emission signals, the method includes irradiating the sample with polarized excitation light. In certain embodiments, the method includes modulating the polarization angle of the emission light from a first polarization angle at which the first set of spatially-dependent emission signals is produced to a second polarization angle at which the second set of spatially-dependent emission signals is produced.

The excitation and/or emission light may be polarized using any convenient polarization devices and methods, including but not limited to, polarization filters, polarization converters, integrated optic polarization rotators, polarizing beamsplitters, dichroic polarizing materials, and the like. In some instances, the excitation and/or emission light is polarized by a polarization device (i.e., a polarizer) which allows light of only a single polarization component to pass. In some cases, polarization of the excitation or emission light is achieved using a polarization filter which passes light of a particular desired polarization and blocks waves of other polarizations. In certain embodiments both the excitation light and the emission light of the polymeric dye is polarized. In some cases, the polarization device is disposed in the excitation pathway that extends from the excitation light source to the sample. In some cases, the polarization device is disposed in the emission pathway that extends from the emission light source to the sample.

The polarization angle of a polarized excitation or emission light is defined by the plane of the polarized light waves and the polarization axis of the light beam, where the angle may be measured relative to any convenient reference point. Modulating the polarization angle of the polarized excitation or emission light leads to a change in the alignment of a polymeric dye molecule's transition dipole moment relative to the electric field vector of the modulated polarized light. When the excitation light is polarized, a change in the polarization angle modulates the extent of absorption of incoming photons by the polymeric dye molecule and thus subsequently effects the emission of light. In some embodiments of the method, the polarizing includes restricting the polarization of incident light at a detector to a first polarization angle. When the emission light is polarized by a polarization device in the pathway between the polymeric dye and the detector, a change in the polarization angle modulates the intensity of incident photons collected at the detector that are originated from a polymeric dye molecule of interest that was aligned with the polarization angle. In certain instances, the method further includes modulating the polarization angle of the incident light at the detector from a first polarization angle to a second polarization angle.

For example, FIG. 3 illustrates a graph showing one possible periodicity of fluorescence intensity over a range of polarization angles from 0 to 360°. As such, a polymeric dye molecule located at a particular spatial location in a sample may have an associated emission signal dependent on the polarization angle. In some embodiments of the method, the polymeric dye is located at a first location in the sample and has a first emission signal at the first polarization angle and a second emission signal at the second polarization angle. In certain cases, the intensity of the second polarized emission signal is 50% or less of the intensity of the first polarized emission signal, such as 45% or less, 40% or less, 35% or less, 30% or less, 25% or less, 20% or less, 15% or less, 10% or less, 5% or less, 2% or less, 1% or less, or even less. In certain embodiments, the range of polarization angles at which a set of spatially dependent emission signals is produced may range over 60 degrees or less, such as over 50 degrees or less, over 40 degrees or less, over 30 degrees or less, over 20 degrees or less, over 18 degrees or less, over 16 degrees or less, over 14 degrees or less, over 12 degrees or less, over 10 degrees or less, over 9 degrees or less, over 8 degrees or less, over 7 degrees or less, over 6 degrees or less, over 5 degrees or less, over 4 degrees or less, over 3 degrees or less, over 2 degrees or less, or over 1 degree or less.

Any convenient method for modulating the polarization angle of a polarized light may be utilized in the subject methods. In some instances, modulating the polarization angle includes rotating a polarization optical element or device in the excitation and/or emission pathway of light. In some cases, a spinning polarizer is modulated to provide for modulation of the polarization angle. Polarization modulators of interest include, but are not limited to, acoustic-optical modulator, electro-optical modulators, magneto-optical modulators and photoelastic modulators. In some instances, the polarization modulator is a Pockels cell, which may be static or rotatable. Rotation of the polarization axis of a linearly polarized light beam relative to the sample may provide for modulation of the polarization angle. In some embodiments of the method, the modulating includes modulating the linear polarization angle of the polarized excitation light in the range of 0 to 360°, such as in the range from 0 to 180°, where the polarization angle is measured relative to any convenient reference angle. The polarization of the excitation or emission light may pass each polarization direction at least once or exactly once, where the polarization is preferably modulated from an initial orientation to an identical orientation at the end of the modulation, where e.g. the modulation rotates a linear polarization exactly once by 180° or by 360°.

The modulating of the polarization angle may be performed continuously and in synchronization with the detecting of the spatially-dependent emission signals. For example, as depicted in FIG. 2A-2B, the polarizer may be rotated continuously to provide for continuous modulation of the polarization angle of the excitation and/or emission light, where the detector may then collect emission signals, e.g., either continuously or at particular intervals. The modulating of the polarization angle may be performed in a stepwise fashion where the polarization angle is changed from a first to a second polarization angle at which it is held while the detector collects spatially dependent emission signals. For example, the polarizer (FIG. 2A-2B) may rotate and stop at discrete steps of 20° or less, such as, steps of 10° or less, steps of 5° or less, steps of 4° or less, steps of 3° or less, steps of 2° or less, steps of 1° or less, or even less.

In certain embodiments of method, the polymeric dye is spatially distributed at a plurality of locations in the sample and at each location emits a distinct emission signal that is dependent on the polarization angle of the polarized excitation light, and/or the polarized emission light. In some instances of the method, the polymeric dye located at a first location in the sample produces at the detector a first polarized emission signal at the first polarization angle and a second polarized emission signal at the second polarization angle. In certain instances, the difference between the first emission signal and the second emission signal corresponds to an intensity for the first location in the high resolution fluorescence image. The polarized emission signals may fluctuate as a function of the polarization angle, depending on the alignment of the polymeric dye molecule from which the signal originates (e.g., as described herein). The spatial point origins of these polarized emission signals may be recorded and integrated to build a high resolution fluorescent image of the sample in the field of view.

Aspects of the method include detecting first and second sets of spatially-dependent emission signals from a sample labeled with a fluorescent polymeric dye. The detecting of the sets of spatially-dependent emission signals may be performed on a timescale that is relatively short compared to the kinetics of the molecular motion of the polymeric dye molecules. The images of multiple detected subsets of polymeric dye molecules may be collected at a variety of polarization angles and integrated or combined to produce a high resolution image of the sample. The emission signals from multiple subsets of polymeric dyes in the sample field of view are collected and integrated to provide a total image of the sample field of view. Any convenient microscopy methods may be utilized in detecting the first and second sets of spatially-dependent emission signals and producing the high resolution image of the sample. Microscopy methods of interest include, but are not limited to, those methods described in Canadian Patent Application 2858270, and Walla et al., "Fluorescence nanoscopy by polarization modulation and polarization angle narrowing", Nature Methods 11, 579-584 (2014).

In some cases, the high resolution fluorescence image is a sub diffraction-limited image of the sample. In certain cases of the method, the imaging includes super-resolution imaging of the sample. Any convenient microscopy methods may be adapted for use in the subject methods to produce a high resolution image of the sample. Microscopy methods of interest include, but are not limited to, those methods which provide for sub diffraction-limited imaging of a sample, such as super-resolution imaging methods including, but not limited to, stochastic optical reconstruction microscopy (STORM), photoactivated localization microscopy (PALM), stimulated emission depletion microscopy (STED) and structured illumination microscopy (SIM) optical antennas, near-field scanning optical microscope (NSOM), near-field optical random mapping (NORM) microscopy, spatially modulated illumination (SMI) microscopy, ground state depletion (GSD), saturated structured illumination microscopy (SSIM), SPDM (Spectral Precision Distance Microscopy), and single-molecule localization microscopy (SMLM).

In some embodiments of the method, the high resolution image of the sample that is produced using the subject methods has a resolution of 500 nm or less, such as 300 nm or less, 250 nm or less, 200 nm or less, 150 nm or less, 100 nm or less, 90 nm or less, 80 nm or less, 70 nm or less, 60 nm or less, 50 nm or less, 40 nm or less, 30 nm or less, 20 nm or less, 10 nm or less, or even less, where the resolution in some instances in 1 nm or more, such as 5 nm or mor. As such, the high resolution image of the sample may be used to distinguish between features of the sample image (e.g., localized polymeric dye conjugated specifically bound to target analytes) that are separated by a distance of 500 nm or less, such as 300 nm or less, 250 nm or less, 200 nm or less, 150 nm or less, 100 nm or less, 90 nm or less, 80 nm or less, 70 nm or less, 60 nm or less, 50 nm or less, 40 nm or less, 30 nm or less, 20 nm or less, 10 nm or less, or even less, and in some instances 1 nm or more, such as 5 nm or more.

The method may further include time lapse imaging of the sample. In some instances, the method further includes repeating the steps of the method one or more times to produce a time lapse image of the sample. In such cases, the method may find use in the investigation of a biological process of interest. The subject method may be repeated as many times as desired at time points of interest over a period of time relevant to the timescale of a particular biological process of interest. The subject method may be performed continuously over a period of time relevant to the timescale of a particular biological process of interest. Alternatively, the method may be repeated at any convenient number of discrete time points over a timescale of interest. In certain embodiments, the method of time lapse imaging of the sample is performed over a period of time of at least 1 minute, such as at least 2 minutes, at least 5 minutes, at least 10 minutes, at least 30 minutes, at least 1 hour, at least 6 hours, at least 12 hours, at least 1 day, or even more.

Multicolor polymeric dyes may be utilized in the subject methods to generate two or more types of emission signals from two or more polymeric dyes of interest, where each polymeric dye may be a probe for a distinct analyte of interest. In certain cases, the sample includes two or more distinct polymer dyes each having distinct and non-overlapping emission wavelengths. A variety of multiplexing and multicolor methods may be utilized to optically analyze a sample of interest. In certain embodiments of the method, the sample includes a first polymeric dye having a first emission maximum wavelength and a second polymeric dye having a second emission maximum wavelength and step (a) includes detecting first and second sets of spatially-dependent emission signals from the sample at first and second emission maximum wavelengths.

Any convenient samples that may be labeled with a polymeric dye may find use in the subject methods of high resolution imaging. Polymeric dyes find use in the analysis of a variety of samples of interest in a variety of applications. As used herein, the term "sample" relates to a material or mixture of materials, in some cases in liquid form, containing one or more analytes of interest. In some embodiments, the sample is a biological sample (e.g., as defined herein). By labeled is meant that the polymeric dye is linked, directly or indirectly, covalently or non-covalently to one or more components of a sample. In certain embodiments, a polymeric dye is utilized as a stain to fluorescently label a component of the sample, e.g., via covalent conjugation of a polymeric dye reagent with the component. A variety of methods of labeling a sample with a polymeric dye may be utilized to fluorescently label the sample, see e.g., the materials and methods described by Greg T. Hermanson in Bioconjugate Techniques, Academic Press, $2^{nd}$ Ed., 2008. In some embodiments, a polymeric dye conjugate (e.g., as described herein) is utilized as a probe, e.g., to specifically bind to a target analyte that is present, or suspected of being present, in the sample.

Aspects of the method include irradiating a sample including a polymeric dye with an excitation light. Any convenient methods for irradiating a sample with an excitation light may be utilized. Devices and methods of interest which may be adapted to irradiate a sample according to the subject methods include, but are not limited to, those devices and methods of fluorescence microscopy, and polarized light microscopy, including methods that involve polarization of incident and/or transmitted light. The excitation light may be provided from any convenient light source. Light sources of interest include, but are not limited to, lasers, photodiodes, and lamps, including mercury or xenon lamps, a flash lamp, incandescent bulb or any other light source suitable for excitation of fluorescence. In certain embodiments of the method, the light source is a laser. In some embodiments of the method, the light source is a coherent source.

In some instances of the method, the light source emits light at a wavelength in the range from 280 nm to 750 nm, including in the range from 300 nm to 400 nm, or in the range from 350 nm to 495 nm, or in the range of 300 and 475 nm. The light source may be selected to provide light of a desired wavelength that is compatible with the absorption spectrum of the polymeric dye of interest in the sample. In certain embodiments, the light source emits light at a wavelength in the range of 280 and 475 nm. In certain embodiments of the method, the light source emits light in the ultraviolet region and the polymeric dye has an absorption maximum wavelength in the ultraviolet region. In some instances of the method, light source emits light in the visible region and the polymeric dye has an absorption maximum wavelength in the visible region.

The excitation light and/or fluorescence from a polymeric dye of interest can be filtered through one or more optical filters. The one or more optical filters can be any suitable optical filter. The optical filter or filters can be placed such that the light irradiated from the light source, or from the polymeric dye, passes through the optical filter before reaching the light detector. The one or more optical filters may be constructed to preferentially transmit the one or more wavelengths of interest.

In some embodiments, irradiation of a polymeric dye molecule of interest is performed for an amount of time sufficient to excite the polymeric dye in the sample without photobleaching the polymeric dye or causing any photodamage to the polymeric dye or to any components of interest in the sample. For example, when the sample is a cell, the irradiating step may be performed for a period of time during and after which the biological activity of the cell and cell components thereof is maintained. In some instances, the irradiation time is 1 second or less, such as 100 ms or less, 50 ms or less, 10 ms or less, or even less. In certain instances of the method, the irradiating is continuous. In some cases of the method, the irradiating is pulsed. In some embodiments of the method, the irradiating includes simultaneously irradiating the entire sample.

High Resolution Cellular Imaging

Aspects of the present disclosure include methods for high resolution imaging of a cell. Any of the methods described herein may be applied to the high resolution imaging of a cell of interest. As such, the sample may be a cellular sample that includes a cell of interest. In some instances of the method, the sample is a cell. As used herein, the term "cell" is used in its conventional sense to refer to the basic structural unit of living organisms, both eukaryotic and prokaryotic, having at least a nucleus and a cell membrane. In certain embodiments, cells include prokaryotic cells, such as from bacteria. In other embodiments, cells include eukaryotic cells, such as cells obtained from biological samples from animals, plants or fungi.

A variety of cells may be targeted for imaging using the subject methods. Target cells of interest include, but are not limited to, stem cells, e.g., pluripotent stem cells, hematopoietic stem cells, T cells, T regulator cells, dendritic cells, B Cells, e.g., memory B cells, antigen specific B cells, granulocytes, leukemia cells, lymphoma cells, virus cells (e.g., HIV cells) NK cells, macrophages, monocytes, fibroblasts, epithelial cells, endothelial cells, and erythroid cells. Target cells of interest include cells that have a convenient cell surface marker or antigen. In some embodiments, the target cell is selected from HIV containing cell, a Treg cell, an antigen-specific T-cell populations, tumor cells or hematopoetic progenitor cells (CD34+) from whole blood, bone marrow or cord blood. Any convenient cell surface proteins, cell markers or intracellular targets may be targeted for specific binding to polymeric dyes (e.g., polymeric dye conjugates) in the subject methods. In some embodiments, the target cell includes a cell surface marker selected from a cell receptor and a cell surface antigen. For example, the target cell may include a cell surface antigen such as CD11b, CD123, CD14, CD15, CD16, CD19, CD193, CD2, CD25, CD27, CD3, CD335, CD36, CD4, CD43, CD45RO, CD56, CD61, CD7, CD8, CD34, CD1c, CD23, CD304, CD235a, T cell receptor alpha/beta, T cell receptor gamma/delta, CD253, CD95, CD20, CD105, CD117, CD120b, Notch4, Lgr5 (N-Terminal), SSEA-3, TRA-1-60 Antigen, Disialoganglioside GD2 and CD71.

In certain instances, the method includes: contacting a cell with a polymeric dye conjugate (e.g., as described herein) that specifically binds a subcellular target under conditions in which the polymeric dye conjugate is localized to the subcellular target location; detecting first and second sets of spatially-dependent emission signals from the sample; and producing a high resolution fluorescence image of the cell from the detected first and second sets of spatially-dependent emission signals.

Any convenient method may be used to contact the cell with a polymeric dye conjugate. In some instances, the sample is contacted with the polymeric dye conjugate under conditions in which the specific binding member of the conjugate specifically binds to the subcellular target of the cell, if present. In some cases, for specific binding of the conjugate to the target cell, an appropriate solution may be used that maintains the viability of the cells. The solution may be a balanced salt solution, e.g., normal saline, PBS, Hank's balanced salt solution, etc., conveniently supplemented with fetal calf serum, human platelet lysate or other factors, in conjunction with an acceptable buffer at low concentration, such as from 5-25 mM (e.g., as described above). The temperature at which specific binding of the conjugate and the target cell takes place may vary, and in some instances may range from 5° C. to 50° C., such as from 10° C. to 40° C., 15° C. to 40° C., 20° C. to 40° C., e.g., 20° C., 25° C., 30° C., 35° C. or 37° C. (e.g., as described above). Any convenient incubation time for specific binding may be selected to allow for the formation of a desirable amount of binding complex (e.g., as described above). In some instances, the cell is a fixed, permeabilized cell.

In some instances of the method, the excitation light is a polarized excitation light and the method includes irradiating the cell with polarized excitation light to produce the first and second spatially-dependent emission signals. In certain instances, the method includes modulating the polarization angle of the polarized excitation light from a first polarization angle at which the first set of spatially-dependent emission signals is produced to a second polarization angle at which the second set of spatially-dependent emission signals is produced. In some embodiments of the method, the polymeric dye is located at a subcellular target location in the sample and has a first emission signal at the first polarization angle and a second emission signal at the second polarization angle.

In certain instances of the method, emission light from the cell is polarized to produce the first and second spatially-dependent emission signals. In some instances of the method, the excitation light is not polarized. In some instances of the method, the excitation light and the emission light is polarized. In some embodiments, the method includes modulating the polarization angle of the emission light at the detector from a first polarization angle at which the first set of spatially-dependent emission signals is produced to a second polarization angle at which the second set of spatially-dependent emission signals is produced. In certain embodiments, the polymeric dye is located at the subcellular target location and produces at the detector a first emission signal at the first polarization angle and a second emission signal at the second polarization angle.

The emission signals may fluctuate as a function of the polarization angle, depending on the alignment of the polymeric dye (e.g., as described herein). The spatial point origins of the first and second sets of spatially dependent emission signals may be recorded and integrated to produce a high resolution fluorescent image of the cell in the field of view. In certain embodiments of the method, the difference between the first polarized emission signal and the second polarized emission signal corresponds to an image intensity for the subcellular target location in the high resolution fluorescence image. Subcellular target locations of interest include, but are not limited to, extracellular space, cytoplasm, nucleus, mitochondria, Golgi apparatus, endoplasmic reticulum (ER), peroxisome, vacuoles, cytoskeleton, nucleoplasm, nucleolus, nuclear matrix and ribosomes.

In some instances, the method further includes determining the spatial location of the subcellular target location in the cell. Any convenient multiplexing and/or multicolor fluorescence microscopy methods may be utilized to simultaneously optically analyze multiple analytes in the cell. In some instances, the method further includes contacting the cell with a second polymeric dye conjugate that specifically binds a second subcellular target and has a second emission wavelength maximum. The fluorescence absorption and emission properties of the first polymeric dye conjugate and the second polymeric dye conjugate may be selected to provide for multicolor detection in two or more detection channels. Such methods may find use in investigating the interaction or connection between two analytes of interest in a cell.

Fluorescent Polymeric Dyes

Fluorescent polymeric dyes find use in a variety of applications, such as labeling a sample of interest. For example, a variety of polymeric dye conjugates that specifically bind to a target analyte are available and may be immobilized at a particular location in a sample where the target analyte is found. Fluorescent polymeric dyes that find use in the subject methods and systems are varied. In some instances of the method, the polymeric dye includes a conjugated polymer. Conjugated polymers (CPs) are characterized by a delocalized electronic structure which includes a backbone of alternating unsaturated bonds (e.g., double and/or triple bonds) and saturated (e.g., single bonds) bonds, where 7-electrons can move from one bond to the other. As such, the conjugated backbone may impart an extended linear structure on the polymeric dye, with limited bond angles between repeat units of the polymer. For example, proteins and nucleic acids, although also polymeric, in some cases do not form extended-rod structures but rather fold into higher-order three-dimensional shapes. In addition, CPs may form "rigid-rod" polymer backbones and experience a limited twist (e.g., torsion) angle between monomer repeat units along the polymer backbone chain. In some instances, the polymeric dye includes a CP that has a rigid rod structure. As summarized above, the structural characteristics of the polymeric dyes can have an effect on the fluorescence properties of the molecules.

Any convenient polymeric dyes may be utilized in the subject methods and systems. In some instances, a polymeric dye is a multichromophore that has a structure capable of harvesting light to amplify the fluorescent output of a fluorophore. In some instances, the polymeric dye is capable of harvesting light and efficiently converting it to emitted light at a longer wavelength. In some cases, the polymeric dye has a light-harvesting multichromophore system that can efficiently transfer energy to nearby luminescent species (e.g., a "signaling chromophore"). Mechanisms for energy transfer include, for example, resonant energy transfer (e.g., Forster (or fluorescence) resonance energy transfer, FRET), quantum charge exchange (Dexter energy transfer) and the like. In some instances, these energy transfer mechanisms are relatively short range; that is, close proximity of the light harvesting multichromophore system to the signaling chromophore provides for efficient energy transfer. Under conditions for efficient energy transfer, amplification of the emission from the signaling chromophore occurs when the number of individual chromophores in the light harvesting multichromophore system is large; that is, the emission from the signaling chromophore is more intense when the incident light (the "excitation light") is at a wavelength which is absorbed by the light harvesting multichromophore system than when the signaling chromophore is directly excited by the pump light.

The multichromophore may be a conjugated polymer. Conjugated polymers (CPs) are characterized by a delocalized electronic structure and can be used as highly responsive optical reporters for chemical and biological targets. Because the effective conjugation length is substantially shorter than the length of the polymer chain, the backbone contains a large number of conjugated segments in close proximity. Thus, conjugated polymers are efficient for light harvesting and enable optical amplification via Forster energy transfer.

Polymeric dyes of interest include, but are not limited to, those dyes described by Gaylord et al. in US Publication Nos. 20040142344, 20080293164, 20080064042, 20100136702, 20110256549, 20120028828, 20120252986 and 20130190193 and U.S. Pat. Nos. 8,575,303 and 8,802,450, the disclosures of which are herein incorporated by reference in their entirety; and Gaylord et al., J. Am. Chem. Soc., 2001, 123 (26), pp 6417-6418; Feng et al., Chem. Soc. Rev., 2010, 39, 2411-2419; and Traina et al., J. Am. Chem. Soc., 2011, 133 (32), pp 12600-12607, the disclosures of which are herein incorporated by reference in their entirety.

In some embodiments, the polymeric dye includes a conjugated polymer including a plurality of first optically active units forming a conjugated system, having a first absorption wavelength (e.g., as described herein) at which the first optically active units absorbs light to form an excited state. In certain instances, the polymeric dye is a multichromophore that includes a conjugated polymer segment or an oligomeric structure including bandgap-lowering n-conjugated repeating units. The conjugated polymer (CP) may be polycationic, polyanionic and/or a charge-neutral conjugated polymer.

The CPs may be water soluble for use in biological samples. Any convenient substituent groups may be included in the polymeric dyes to provide for increased water-solubility, such as a hydrophilic substituent group, e.g., a hydrophilic polymer, or a charged substituent group, e.g., groups that are positively or negatively charged in an aqueous solution, e.g., under physiological conditions. Any convenient water-soluble groups (WSGs) may be utilized in the subject light harvesting multichromophores. The term "water-soluble group" refers to a functional group that is well solvated in aqueous environments and that imparts improved water solubility to the molecules to which it is attached. While the increase in solubility may vary, in some instances the increase (as compared to the compound without the WSG(s)) is 2 fold or more, e.g., 5 fold, 10 fold, 25 fold, 50 fold, 100 fold or more. In some embodiments, a WSG increases the solubility of the multichromophore in a predominantly aqueous solution (e.g., as described herein), as compared to a multichromophore which lacks the WSG. The water soluble groups may be any convenient hydrophilic group that is well solvated in aqueous environments. In some cases, the hydrophilic water soluble group is charged, e.g., positively or negatively charged. In certain cases, the hydrophilic water soluble group is a neutral hydrophilic group. In some embodiments, the WSG is a hydrophilic polymer, e.g., a polyethylene glycol, a cellulose, a chitosan, or a derivative thereof.

As used herein, the terms "polyethylene oxide", "PEO", "polyethylene glycol" and "PEG" are used interchangeably and refer to a polymer including a chain described by the formula $—(CH_2—CH_2—O—)_n—$ or a derivative thereof. In some embodiments, "n" is 5000 or less, such as 1000 or less, 500 or less, 200 or less, 100 or less, 50 or less, 40 or less, 30 or less, 20 or less, 15 or less, such as 5 to 15, or 10 to 15. It is understood that the PEG polymer may be of any convenient length and may include a variety of terminal groups, including but not limited to, alkyl, aryl, hydroxyl, amino, acyl, acyloxy, and amido terminal groups. Functionalized PEGs that may be adapted for use in the subject multichromophores include those PEGs described by S. Zalipsky in "Functionalized poly(ethylene glycol) for preparation of biologically relevant conjugates", Bioconjugate Chemistry 1995, 6 (2), 150-165. Water soluble groups of interest include, but are not limited to, carboxylate, phosphonate, phosphate, sulfonate, sulfate, sulfinate, ester, polyethylene glycols (PEG) and modified PEGs, hydroxyl, amine, ammonium, guanidinium, polyamine and sulfonium, polyalcohols, straight chain or cyclic saccharides, primary, secondary, tertiary, or quaternary amines and polyamines, phosphonate groups, phosphinate groups, ascorbate groups, glycols, including, polyethers, —COOM', —SO$_3$M', —PO$_3$M', —NR$_3^+$, Y', (CH$_2$CH$_2$O)$_p$R and mixtures thereof, where Y' can be any halogen, sulfate, sulfonate, or oxygen containing anion, p can be 1 to 500, each R can be independently H or an alkyl (such as methyl) and M' can be a cationic counterion or hydrogen, —(CH$_2$CH$_2$O)$_{yy}$CH$_2$CH$_2$XR$^{yy}$, —(CH$_2$CH$_2$O)$_{yy}$CH$_2$CH$_2$X—, —X(CH$_2$CH$_2$O)$_{yy}$CH$_2$CH$_2$—, glycol, and polyethylene glycol, wherein yy is selected from 1 to 1000, X is selected from O, S, and NR$^{zz}$, and R$^{zz}$ and R$^{YY}$ are independently selected from H and C1-3 alkyl. In some cases, a WSG is (CH$_2$)$_x$(OCH$_2$CH$_2$)$_y$OCH$_3$ where each x is independently an integer from 0-20, each y is independently an integer from 0 to 50.

Multiple WSGs may be included at a single location in the subject multichromophores via a branching linker. In certain embodiments, the branching linker is an aralkyl substituent, further di-substituted with water solubilizing groups. As such, in some cases, the branching linker group is a substituent of the multichromophore that connects the multichromophore to two or more water solubilizing groups. In some cases, the incorporation of multiple WSGs via branching linkers imparts a desirable solubility on the multichromophore. In some instances, the WSG is a non-ionic sidechain group capable of imparting solubility in water in excess of 10 mg/mL.

In some embodiments, the multichromophore includes substituent(s) selected from the group consisting of, an alkyl, an aralkyl and a heterocyclic group, each group further substituted with a include water solubilizing groups hydrophilic polymer group, such as a polyethylglycol (PEG) (e.g., a PEG group of 2-20 units).

The polymeric dye may have any convenient length. In some cases, the particular number of monomeric repeat units or segments of the polymeric dye may fall within the range of 2 to 500,000, such as 2 to 100,000, 2 to 30,000, 2 to 10,000, 2 to 3,000 or 2 to 1,000 units or segments, or such as 100 to 100,000, 200 to 100,000, or 500 to 50,000 units or segments. In some instances, the particular number of monomeric repeating units or segments of the multichromophore may fall within the range of 2 to 1,000, such as 2 to 500, 2 to 100, 3 to 100, 4 to 100, 5 to 100, 6 to 100, 7 to 100, 8 to 100, 9 to 100 or 10 to 100 units or segments.

The polymeric dyes may be of any convenient molecular weight (MW). In some cases, the MW of the polymeric dye may be expressed as an average molecular weight. the In some instances, the polymeric dye has an average molecular weight of from 500 to 500,000, such as from 1,000 to 100,000, from 2,000 to 100,000, from 10,000 to 100,000 or even an average molecular weight of from 50,000 to 100,000. In certain embodiments, the polymeric dye has an average molecular weight of 70,000.

The subject polymeric dyes may include a multichromophore that comprises one or more co-monomers selected from a phenylenevinylene co-monomer, a phenyleneethynylene co-monomer, a fused 6-5-6 tricyclic co-monomer, a fluorene co-monomer, a carbazole co-monomer, a C$_2$-C$_{12}$ alkyne co-monomer, an arylene-ethynylene co-monomer, a heteroarylene-ethynylene co-monomer, an arylene co-monomer and a heteroarylene co-monomer. In some instances, the polymeric dye includes a phenylenevinylene-based multichromophore (e.g., a conjugated polymer including at least 50 mol % of phenylenevinylene co-monomers). In some instances, the polymeric dye includes a phenyleneethynylene-based multichromophore (e.g., a conjugated polymer including at least 50 mol % of phenyleneethynylene co-monomers). In some instances, the polymeric dye includes a carbazole-based multichromophore (e.g., a conjugated polymer including at least 50 mol % of carbazole co-monomers). In some instances, the polymeric dye includes a fluorene-based multichromophore (e.g., a conjugated polymer including at least 50 mol % of fluorene co-monomers). In some instances, the polymeric dye includes a C$_2$-C$_{12}$ alkyne-based multichromophore (e.g., a conjugated polymer including at least 50 mol % of C$_2$-C$_{12}$ alkyne co-monomers). In some instances, the polymeric dye includes an arylene- or heteroarylene-ethynylene-based multichromophore (e.g., a conjugated polymer including at least 50 mol % of arylene- or heteroarylene-ethynylene co-monomers). In some instances, the polymeric dye includes an arylene- or heteroarylene-based multichromophore (e.g., a conjugated polymer including at least 50 mol % of arylene- or heteroarylene-co-monomers). In certain instances, in addition to the co-monomers described above, the multichromophore includes a linking co-monomer that has a linking group to which may be attached any convenient moieties of interest (e.g., a linked acceptor chromophore or a specific binding member).

It is understood that in some cases the subject multichromophores may include co-blocks (e.g., n and m co-blocks). The subject multichromophores may include any convenient linear arrangements of n and m co-blocks of various lengths within the structure of the overall polymer. In addition, the multichromophores may include any convenient arrangements of co-monomers within such n and/or m co-blocks. A variety of polymer synthesis methods may be utilized to prepare co-monomers and co-blocks of interest in the preparation of the subject multichromophores. It is understood that in some cases, the polymerization methods may produce a composition including a population of conjugated polymers that includes some variation with respect to the particular length and/or terminal groups (i.e., end groups) present in each conjugated polymer of the population. The formulae depicted herein may refer to a single compound or to a population or sub-population of polymeric compounds.

In certain instances, the polymeric dye includes the following structure:

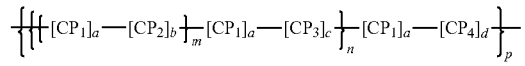

wherein CP$_1$, CP$_2$, CP$_3$ and CP$_4$ are independently a conjugated polymer segment or an oligomeric structure, wherein one or more of CP$_1$, CP$_2$, CP$_3$ and CP$_4$ are bandgap-lowering n-conjugated repeat units. In some cases, one or more of CP$_1$, CP$_2$, CP$_3$ and CP$_4$ are fused 6-5-6 tricyclic co-monomers. A fused 6-5-6 tricyclic co-monomer is a co-monomer including a tricyclic aromatic group having three fused rings in the configuration 6-5-6, i.e. two benzo ring fused to a central 5 membered ring. The 5-membered ring can be a carbocycle or a heterocycle and can further include a sidechain substituent at the ring atom that is not fused to a benzo ring (i.e., at Y$^1$). In certain instances, the fused 6-5-6 tricyclic co-monomer that finds use in the subject multichromophore is described by the following formula (XI):

(XI)

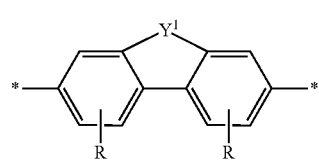

where:

$Y^1$ is —$C(R^1)_2$— or —$N(R^1)$—;

each R is independently H or one or more substituents (e.g., as described herein); and each $R^1$ is independently selected from the group consisting of an alkyl, a substituted alkyl, an aralkyl, a substituted aralkyl, a PEG moiety and -$L^1$-$Z^2$, where $L^1$ is a linker and $Z^2$ is a chemoselective tag (e.g., a tag including a chemoselective functional group), a WSG or a linked acceptor chromophore. In some embodiments, when $Y^1$ is —$N(R^1)$—, the fused 6-5-6 tricyclic co-monomer is a carbazole co-monomer. Any convenient carbazole co-monomers may be utilized in the subject multichromophores. In some embodiments, when $Y^1$ is —$C(R^1)_2$—, the fused 6-5-6 tricyclic co-monomer is a fluorene co-monomer. Any convenient fluorene co-monomers may be utilized in the subject multichromophores.

A fluorene co-monomer is a co-monomer including an aromatic group having a 9H-fluorene core structure substituted at the 9 position with any convenient sidechain substituent(s). In some cases, the fluorene co-monomer is a 9,9-disubstituted fluorene. The fluorene co-monomer is conjugated to adjacent polymeric backbone groups via any convenient positions of the fluorene core structure, such as any two positions of positions 1-8 (see numbering scheme below). In some embodiments, the fluorene core structure is linked to adjacent groups of the polymer backbone via the 2 and 7 positions. In certain embodiments, the fluorene co-monomer is described by the following formula (XII):

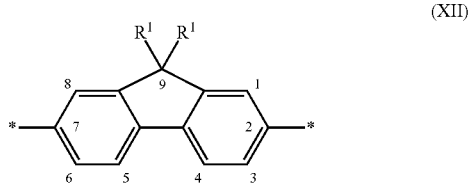

(XII)

where: each $R^1$ is independently selected from an alkyl, a substituted alkyl, an aralkyl, a substituted aralkyl, a PEG moiety and -$L^2$-$Z^2$, where $L^2$ is a linker and $Z^2$ is a chemoselective tag (e.g., a tag including a chemoselective functional group), a WSG or an acceptor chromophore. In some cases, $Z^2$ is a chemoselective tag that finds use in covalently linking the multichromophore to an acceptor chromophore (e.g., as described herein). In certain embodiments, $L^2$ is a branched linker (e.g., a substituted benzyl group) that links to two or more $Z^2$ groups (e.g., WSGs such as PEG groups of 2-20 polyethylene glycol units). As used in the formula herein, * denotes a site for covalent attachment to unsaturated backbone of a conjugated polymer or a terminal group.

In certain instances, the fluorene co-monomer is described by the formula (XIII):

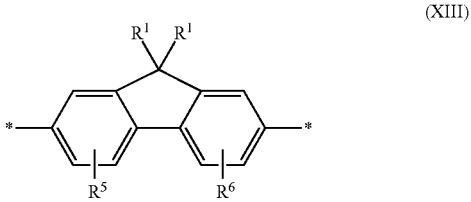

(XIII)

where: each $R^1$ is as defined above; and $R^5$ and $R^6$ are independently selected from H, a water solubilizing group (WSG), or an aryl substituent (e.g., as described herein). In some instances, the fluorene co-monomer is described by the formula (XIV):

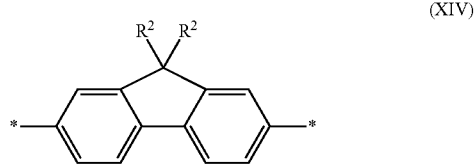

(XIV)

where each $R^2$ is a alkyl substituted with a water solubilizing group or a branched linker connected to two or more water solubilizing groups (e.g., a PEG-disubstituted benzyl or a PEG substituted alkyl). In certain embodiments, the fluorene co-monomer is described by the following formula (XV):

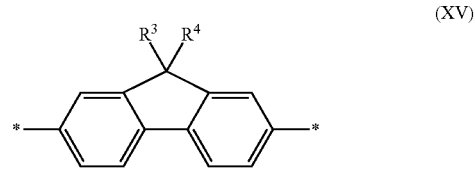

(XV)

where $R^3$ is an alkyl or an aralkyl substituted with a water solubilizing group (e.g., a PEG substituted alkyl or aralkyl), and $R^4$ is $L^2$-$Z^2$ wherein $L^2$ is a linker and $Z^2$ is a chemoselective tag or a linked acceptor chromophore. In some instances, the fluorene co-monomer is described by the formula (XVI):

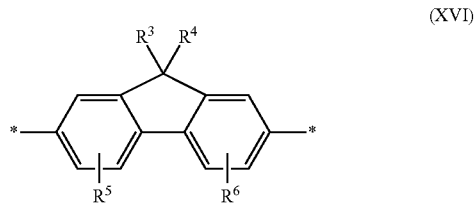

(XVI)

wherein:

$R^3$ is a substituent comprising a water solubilizing group;

$R^4$ is $L^2$-$Z^2$ wherein $L^2$ is a linker and $Z^2$ is a chemoselective tag (e.g., for conjugation to an acceptor chromophore); and $R^5$ and $R^6$ are independently selected from H, a water solubilizing group and an aryl substituent (e.g., an alkyl, a substituted alkyl, an alkoxy, a substituted alkoxy, a halogen or a nitro).

As used herein, the terms "chemoselective functional group" and "chemoselective tag" are used interchangeably and refer to a functional group that can selectively react with another compatible functional group to form a covalent bond, in some cases, after optional activation of one of the functional groups. Chemoselective functional groups of interest include, but are not limited to, thiols and maleimide or iodoacetamide, amines and carboxylic acids or active esters thereof, as well as groups that can react with one another via Click chemistry, e.g., azide and alkyne groups (e.g., cyclooctyne groups), as well as hydroxyl, hydrazido, hydrazino, aldehyde, ketone, azido, alkyne, phosphine, epoxide, and the like.

Any convenient linking co-monomers ($L^1$) may be incorporated into the subject multichromophores to provide for a linking group to which may be attached any convenient moieties of interest (e.g., a linked acceptor chromophore). Linking co-monomers of interest include, but are not limited to, a fluorene co-monomer (e.g., as described herein), a phenylenevinylene co-monomer, a phenyleneethynylene co-monomer, a carbazole co-monomer, a $C_2$-$C_{12}$ alkyne co-monomer, an arylene-ethynylene co-monomer, a heteroarylene-ethynylene co-monomer, an arylene co-monomer and a heteroarylene co-monomer.

Any convenient chemoselective functional groups may be included in the subject multichromophores (e.g., at the —$Z^2$ and/or in the $G^1$ or $G^2$ terminal groups, including, but are not limited to, carboxylic acid, active ester (e.g., NHS or sulfo-NHS ester), amino, hydroxyl, thiol, maleimide, iodoacetyl, hydrazido, hydrazino, aldehyde, ketone, azido, alkyne, phosphine and epoxide. It is understood that in the polymeric dye structures described herein, in some cases, the groups $Z^1$ and $Z^2$ appear at a equivalent position in the structure where these groups can be used interchangeably to refer to either a linked acceptor chromophore or a chemoselective functional group that is capable of subsequent conjugation to an acceptor chromophore to produce the linked acceptor chromophore.

In certain cases, the linking co-monomer is a substituted aryl co-monomer. In certain cases, the linking co-monomer is a substituted heteroaryl co-monomer. In certain cases, the linking co-monomer is a substituted or unsubstituted 1,4-phenyl, a substituted or unsubstituted 1,3-phenyl, a substituted or unsubstituted 4,4'-biphenyl, a substituted or unsubstituted 2,5-pyridyl, and a substituted or unsubstituted 2,6-pyridyl. In some instances, the linking co-monomer is a fluorene co-monomer.

Any convenient end groups (e.g., $G^1$ and $G^2$) may be utilized at the terminals of the subject multichromophores. As used herein, the terms "end group" and "terminal group" are used interchangeably to refer to the groups located at the terminals of the polymeric structure of the multichromophore, e.g., as described herein. $G^1$ and $G^2$ groups of interest include, but are not limited to a terminal capping group, a π conjugated segment, a linker and a linked specific binding member. In some embodiments, a terminal capping groups is a monovalent group which is conjugated to the backbone of the multichromophore after polymerization. In certain instances, the terminal capping group is an aryl, a substituted aryl, a heteroaryl, a substituted heteroaryl, an alkyl or a substituted alkyl. In certain cases, the terminal capping group is derived from a monomer used in the method of polymerization, e.g., a terminal group such as a halogen (e.g., Br), a boronic acid or a boronic ester, which is capable of undergoing further conjugation. In some instances, $G^1$ and/or $G^2$ is a 7C conjugated segment. As used herein, a π conjugated segment refers to any convenient segment of a conjugated polymer to which the multichromophore may be conjugated, i.e., allowing delocalization of pi electron across adjacent units. In certain embodiments, $G^1$ and/or $G^2$ is a linker, such as a linker including a functional group suitable for conjugation to a specific binding moiety. It is understood that linkers located at the $G^1$ and/or $G^2$ positions of the multichromophore may be selected so as to be orthogonal to any other linkers including chemoselective tags that may be present at a sidechain of the multichromophore (e.g., at $Z^2$). In certain embodiments, an amino functional group or derivative thereof is included at $G^1$ and/or $G^2$ and a carboxylic acid functional group or derivative thereof is included at $Z^2$. In certain embodiments, a carboxylic acid functional group or derivative thereof is included at $G^1$ and/or $G^2$ and an amino functional group or derivative thereof is included at $Z^2$.

In some embodiments, the co-monomer is an optionally substituted aryl or heteroaryl co-monomer. Any convenient aryl or heteroaryl co-monomers may be utilized in the subject multichromophores as absorbance-modifying co-monomers. The absorbance-modifying co-monomer or band gap modifying unit may be evenly or randomly distributed along the conjugated polymer. In certain embodiments, the absorbance-modifying co-monomer is an optionally substituted co-monomer selected from 2,1,3-benzothiadiazole, 2,1,3-benzoxadiazole, benzoxidazole, benzoselenadiazole, benzotellurodiazole, naphthoselenadiazole, 4,7-di(thien-2-yl)-2,1,3-benzothiadiazole, squaraine dyes, quinoxalines, perylene, perylene diimides, diketopyrrolopyrrole, thienopyrazine low bandgap commercial dyes, olefins, and cyano-substituted olefins and isomers thereof.

In some instances, aryl and heteroaryl co-monomers which find use in the subject multichromophores are selected from a'-k' having the structure:

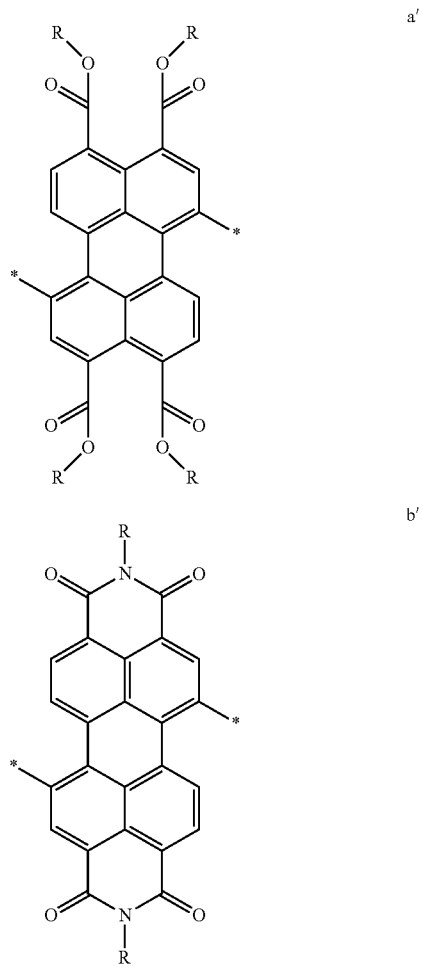

27
-continued
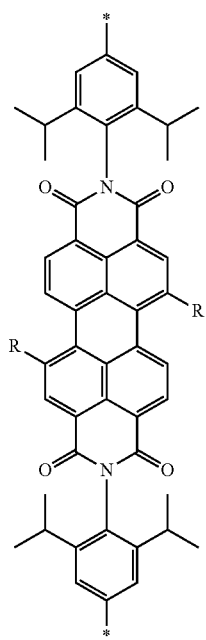
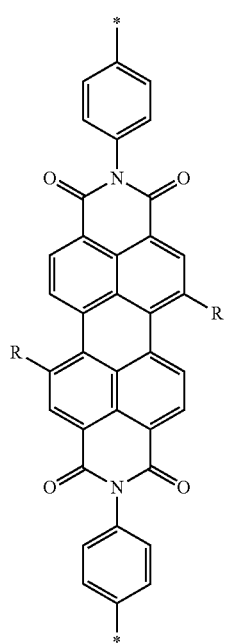
28
-continued
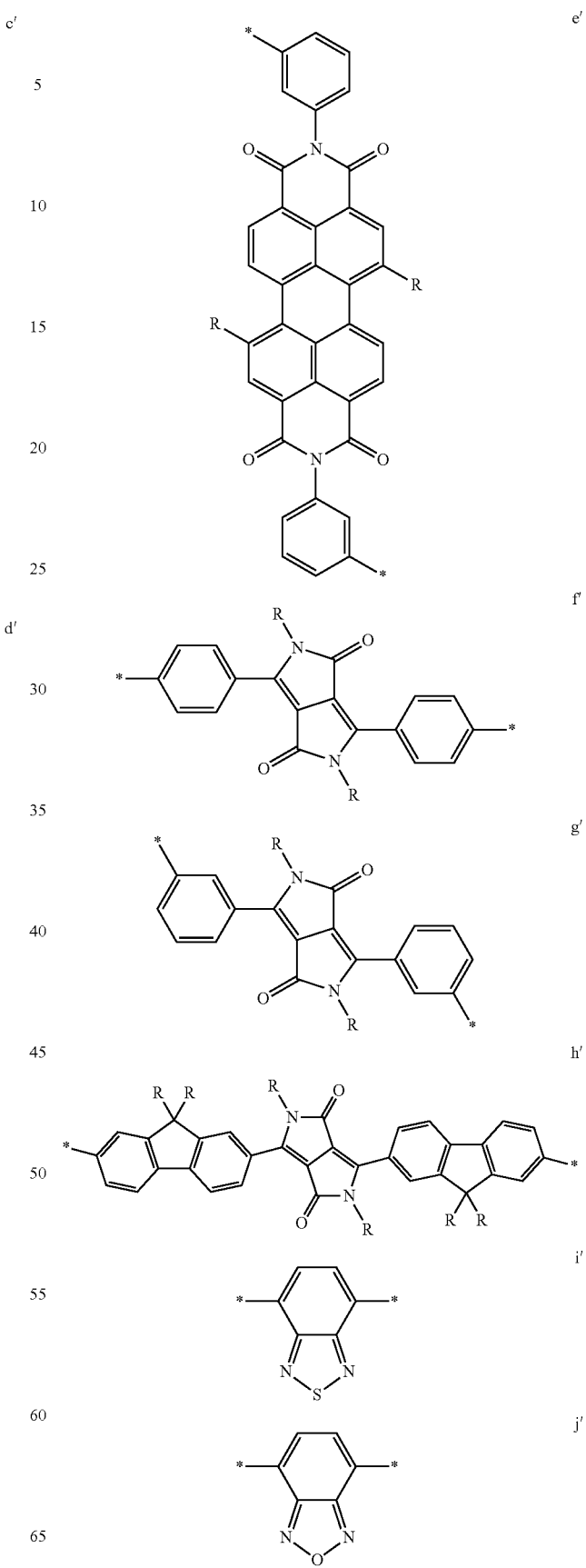

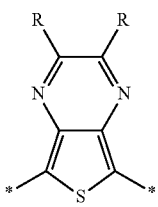

wherein *=a site for covalent attachment to unsaturated backbone and each R is independently H, a non-ionic side group capable of imparting solubility in water (e.g., a WSG), or -L²-Z², where L² is a linker and Z² is a chemoslective tag or a linked acceptor chromophore. In certain instances of a'-k', each R is an alkyl or a benzyl substituted with one or more $(CH_2)_x(OCH_2CH_2)_yOCH_3$ where each x is independently an integer from 0-20, each y is independently an integer from 0 to 50. In certain instances of a'-k', each R is $(CH_2)_3(OCH_2CH_2)OCH_3$.

In certain embodiments, the multichromophore of formula (I) includes an absorbance-modifying co-monomer having the structure of one of co-monomers a'-k', as described herein. In some embodiments, the multichromophore of formula (I) includes an absorbance-modifying co-monomer having the formula (XVIII):

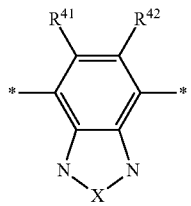

(XVIII)

where X is O or S, $R^{41}$ and $R^{42}$ are each independently, H, halogen, a WSG, an alkyl, a substituted alkyl, an alkoxy and a substituted alkoxy. In certain instances, X is O. In some instances, X is S. In certain embodiments, the absorbance-modifying co-monomer is selected from one of the following:

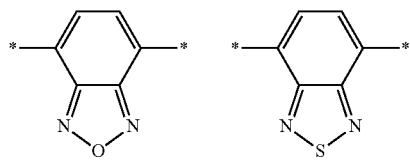

wherein *=site for covalent attachment to unsaturated backbone.

In some instances, the absorbance-modifying co-monomer is a substituted or unsubstituted phenyl, biphenyl or pyridyl co-monomer. In certain embodiments, the absorbance-modifying co-monomer is an optionally substituted aryl or heteroaryl co-monomer selected from the group consisting of substituted or unsubstituted 1,4-phenyl, a substituted or unsubstituted 1,3-phenyl, a substituted or unsubstituted 4,4'-biphenyl, a substituted or unsubstituted 2,5-pyridyl, and a substituted or unsubstituted 2,6-pyridyl.

In some instances, the polymeric dye includes the following structure:

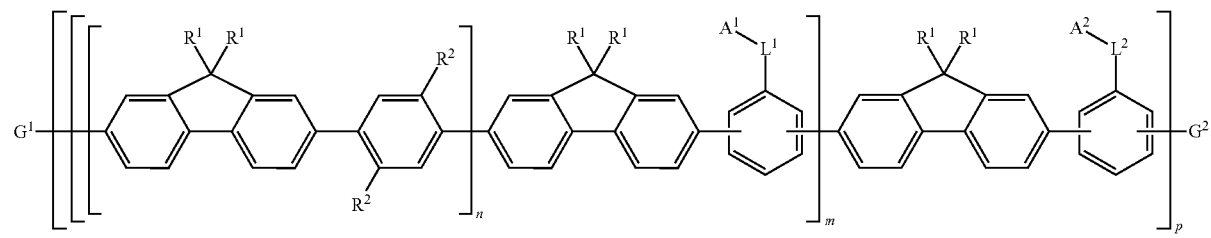

wherein each $R^1$ is independently a solubilizing group or a linker-dye; $L^1$ and $L^2$ are optional linkers; each $R^2$ is independently H or an aryl substituent; each $A^1$ and $A^2$ is independently H, an aryl substituent or a fluorophore; $G^1$ and $G^2$ are each independently selected from the group consisting of a terminal group, a π conjugated segment, a linker and a linked specific binding member; each n and each m are independently 0 or an integer from 1 to 10,000; and p is an integer from 1 to 100,000. Solubilizing groups of interest include alkyl, aryl and heterocycle groups further substituted with a hydrophilic group such as a polyethylglycol (e.g., a PEG of 2-20 units), an ammonium, a sulphonium, a phosphonium, and the like.

In some cases, the polymeric dye includes, as part of the polymeric backbone, a conjugated segment having one of the following structures:

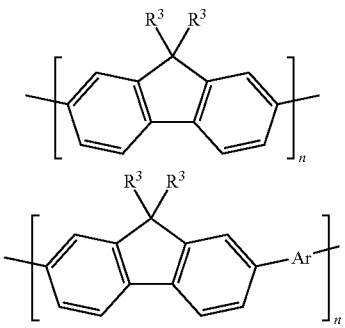

where each $R^3$ is independently an optionally substituted alkyl or aryl group; Ar is an optionally substituted aryl or heteroaryl group; and n is 1 to 10000. In certain embodiments, $R^3$ is an optionally substituted alkyl group. In certain embodiments, $R^3$ is an optionally substituted aryl group. In some cases, $R^3$ is substituted with a polyethyleneglycol, a dye, a chemoselective functional group or a specific binding moiety. In some cases, Ar is substituted with a polyethyleneglycol, a dye, a chemoselective functional group or a specific binding moiety.

In some instances, the polymeric dye includes the following structure:

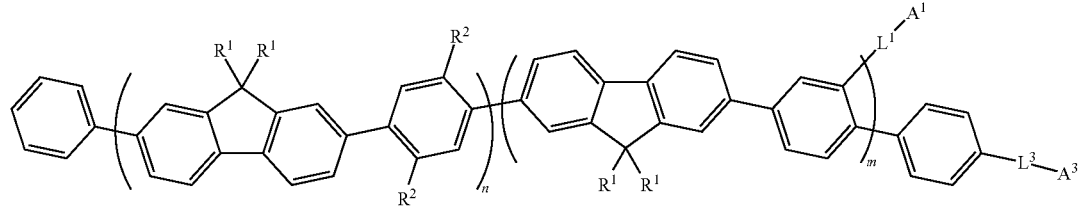

wherein: each $R^1$ is a solubilizing group or a linker-dye group; each $R^2$ is independently H or an aryl substituent; $L_1$ and $L_2$ are optional linkers; each $A^1$ and $A^3$ are independently H, a fluorophore, a functional group or a specific binding moiety (e.g., an antibody); and n and m are each independently 0 to 10000, wherein n+m>1.

The polymeric dye may have one or more desirable spectroscopic properties, such as a particular absorption maximum wavelength, a particular emission maximum wavelength, extinction coefficient, quantum yield, and the like (see e.g., Chattopadhyay et al., "Brilliant violet fluorophores: A new class of ultrabright fluorescent compounds for immunofluorescence experiments." Cytometry Part A, 81A (6), 456-466, 2012).

In some embodiments, the polymeric dye has an absorption curve between 280 and 475 nm. In certain embodiments, the polymeric dye has an absorption maximum in the range 280 and 475 nm. In some embodiments, the polymeric dye absorbs incident light having a wavelength in the range between 280 and 475 nm. In some embodiments, the polymeric dye has an emission maximum wavelength ranging from 400 to 850 nm, such as 415 to 800 nm, where specific examples of emission maxima of interest include, but are not limited to: 421 nm, 510 nm, 570 nm, 602 nm, 650 nm, 711 nm and 786 nm. In some instances, the polymeric dye has an emission maximum wavelength in a range selected from the group consisting of 410-430 nm, 500-520 nm, 560-580 nm, 590-610 nm, 640-660 nm, 700-720 nm and 775-795 nm. In certain embodiments, the polymeric dye has an emission maximum wavelength of 421 nm. In some instances, the polymeric dye has an emission maximum wavelength of 510 nm. In some cases, the polymeric dye has an emission maximum wavelength of 570 nm. In certain embodiments, the polymeric dye has an emission maximum wavelength of 602 nm. In some instances, the polymeric dye has an emission maximum wavelength of 650 nm. In certain cases, the polymeric dye has an emission maximum wavelength of 711 nm. In some embodiments, the polymeric dye has an emission maximum wavelength of 786 nm. In certain instances, the polymeric dye has an emission maximum wavelength of 421 nm±5 nm. In some embodiments, the polymeric dye has an emission maximum wavelength of 510 nm±5 nm. In certain instances, the polymeric dye has an emission maximum wavelength of 570 nm±5 nm. In some instances, the polymeric dye has an emission maximum wavelength of 602 nm±5 nm. In some embodiments, the polymeric dye has an emission maximum wavelength of 650 nm±5 nm. In certain instances, the polymeric dye has an emission maximum wavelength of 711 nm±5 nm. In some cases, the polymeric dye has an emission maximum wavelength of 786 nm±5 nm. In certain embodiments, the polymeric dye has an emission maximum selected from the group consisting of 421 nm, 510 nm, 570 nm, 602 nm, 650 nm, 711 nm and 786 nm.

In some instances, the polymeric dye has an extinction coefficient of $1\times10^6$ cm$^{-1}$M$^{-1}$ or more, such as $2\times10^6$ cm$^{-1}$M$^{-1}$ or more, $2.5\times10^6$ cm$^{-1}$M$^{-1}$ or more, $3\times10^6$ cm$^{-1}$M$^{-1}$ or more, $4\times10^6$ cm$^{-1}$M$^{-1}$ or more, $5\times10^6$ cm$^{-1}$M$^{-1}$ or more, $6\times10^6$ cm$^{-1}$M$^{-1}$ or more, $7\times10^6$ cm$^{-1}$M$^{-1}$ or more, or $8\times10^6$ cm$^{-1}$M$^{-1}$ or more. In certain embodiments, the polymeric dye has a quantum yield of 0.05 or more, such as 0.1 or more, 0.15 or more, 0.2 or more, 0.25 or more, 0.3 or more, 0.35 or more, 0.4 or more, 0.45 or more, 0.5 or more, or even more. In certain cases, the polymeric dye has a quantum yield of 0.1 or more. In certain cases, the polymeric dye has a quantum yield of 0.3 or more. In certain cases, the polymeric dye has a quantum yield of 0.5 or more. In some embodiments, the polymeric dye has an extinction coefficient of $1\times10^6$ or more and a quantum yield of 0.3 or more. In some embodiments, the polymeric dye has an extinction coefficient of $2\times10^6$ or more and a quantum yield of 0.5 or more.

Polymeric Tandem Dyes

In certain embodiments, the polymeric dye is a polymeric tandem dye. Polymeric tandem dyes may include two covalently linked moieties: a donor light harvesting multichromophore (e.g., as described herein) and an acceptor chromophore. In certain instances, the acceptor chromophore is an acceptor dye. In certain instances, the acceptor chromophore is a fluorophore. A polymeric tandem dye may be excited at the excitation wavelength of the donor and may emit at the emission wavelength of the acceptor dye. Any convenient fluorophore may be utilized in the polymeric tandem dyes as an acceptor. Fluorophores of interest include, but are not limited to, fluorescent dyes such as fluorescein, 6-FAM, rhodamine, Texas Red, tetramethylrhodamine, carboxyrhodamine, carboxyrhodamine 6G, carboxyrhodol, carboxyrhodamine 110, Cascade Blue, Cascade Yellow, coumarin, Cy2, Cy3, Cy3.5, Cy5, Cy5.5, Cy-Chrome, phycoerythrin, PerCP (peridinin chlorophyll-a Protein), PerCP-Cy5.5, JOE (6-carboxy-4',5'-dichloro-2',7'-dimethoxyfluorescein), NED, ROX (5-(and-6)-carboxy-X-rhodamine), HEX, Lucifer Yellow, Marina Blue, Oregon Green 488, Oregon Green 500, Oregon Green 514, Alexa Fluor 350, Alexa Fluor 430, Alexa Fluor 488, Alexa Fluor 532, Alexa Fluor 546, Alexa Fluor 568, Alexa Fluor 594, Alexa Fluor 633, Alexa Fluor 647, Alexa Fluor 660, Alexa Fluor 680, Alexa Fluor 700, 7-amino-4-methylcoumarin-3-acetic acid, BODIPY FL, BODIPY FL-Br.sub.2, BODIPY 530/550, BODIPY 558/568, BODIPY 564/570, BODIPY 576/589, BODIPY 581/591, BODIPY 630/650, BODIPY 650/665, BODIPY R6G, BODIPY TMR, BODIPY TR, conjugates thereof, and combinations thereof. Lanthanide chelates of interest include, but are not limited to, europium chelates, terbium chelates and samarium chelates. In some embodiments, the polymeric tandem dye includes a polymeric dye linked to an acceptor fluorophore selected from the group consisting of Cy3, Cy3.5, Cy5, Cy5.5, Cy7, Alexa488, Alexa 647 and Alexa700.

In some instances, the polymeric tandem dye is described by formula (I):

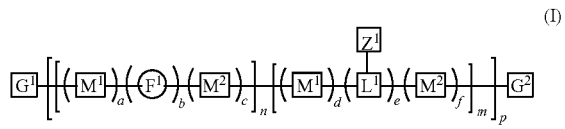

(I)

where:
F$^1$ is a fused 6-5-6 tricyclic co-monomer co-monomer;
each M$^1$ and M$^2$ are each independently a co-monomer;
L$^1$ is a linking co-monomer substituted with an optional acceptor chromophore Z$^1$;
e is 1;
a, b, c, d and f are each independently 0 or 1, wherein a+b+c+d+f≥1;
each n is 0 or an integer from 1 to 100,000;
each m is 0 or an integer from 1 to 10,000;
p is an integer from 1 to 100,000; and
G$^1$ and G$^2$ are each independently selected from a terminal group, a π conjugated segment, a linker and a linked specific binding member. In some instances of formula (I), F$^1$ is a fluorene co-monomer. In some instances of formula (I), F$^1$ is a carbazole co-monomer. In some cases of formula (I), L$^1$ is a fluorene co-monomer. In certain embodiments of formula (I), L$^1$ is a carbazole co-monomer. In some instances of formula (I), L$^1$ is a fluorene co-monomer. In some instances of formula (I), M$^1$ is a fluorene co-monomer. In some cases of formula (I), the linking co-monomer is a fluorene co-monomer. In certain embodiments of formula (I), is an aryl or heteroaryl co-monomer. In certain embodiments of formula (I), M$^1$ is an aryl or heteroaryl co-monomer. In certain embodiments of formula (I), M$^2$ is an aryl or heteroaryl co-monomer.

In some embodiments of formula (I), b is 1. In some instances of formula (X), a is 0. In some cases of formula (I), c is 0. In some instances of formula (I), a is 1. In some cases of formula (I), c is 1. In some instances of formula (I), a+c is ≥1. In certain embodiments of formula (I), d is 0. In certain cases of formula (I), f is 0. In certain embodiments of formula (I), d is 1. In certain cases of formula (I), f is 1. In some instances of formula (I), d+f is ≥1. In some embodiments of formula (I), a+c+d+f=1 (i.e., a is 1, cis 1, d is 1 orf is 1). In some embodiments of formula (I), a+c+d+f=2. In some embodiments of formula (I), a+c+d+f=3. In some embodiments of formula (I), a+c+d+f=4. In certain embodiments of formula (I), e is 1 and d or f is 1, such that d+e+f=2. In certain instances of formula (I), e is 1 and d and f are each 0. In certain instances, e is 1, d+f≤1 and m≥1. In certain instances, e is 1, d and f are each 0 and m≥1. In certain instances, e is 1; d+f=1 and m 1. In some cases, d is 1 and f is 0. In some cases, d is 0 and f is 1. In some embodiments of formula (I), n, m and p are selected such that the multichromophore includes 2 to 100,000 repeat units (i.e., monomeric repeat units) in total, where the multichromophore may include a variety of distinct monomeric repeat units. In some instances, when m is 0, p is 1 and n is 2 to 100,000. In some embodiments of formula (I), L$^1$ is a fluorene co-monomer. It is understood that the conjugated polymer of formula (I) can also be represented by a formula that provides mol % values for each co-monomer in the polymer.

In some embodiments of formula (I), a, c, d and f are each 0 and b and e are each 1. In certain embodiments of formula (I), F$^1$ is a fluorene co-monomer of formula (XIV) as described herein, where each R$^2$ is independently an alkyl substituted with a water solubilizing group, such as each R$^2$ is —(CH$_2$)x(OCH$_2$CH$_2$)yOCH$_3$ where each x is independently 0 or an integer from 1-20, each y is independently 0 or an integer from 1 to 50. In certain embodiments of formula I), L$^1$ is a fluorene co-monomer of formula (XV) as described herein. In some embodiments of formula (I), at least one of G$^1$ and G$^2$ is a substituted aryl group, e.g., an aryl group substituted with a linker (e.g., a C1-C6 alkyl linker) terminated with a carboxylic acid functional group.

In some instances of formula (I): a, c, d and f are each 0 and b and e are each 1; F$^1$ is a fluorene co-monomer of formula (XIV) where each R$^2$ is independently an alkyl substituted with a water solubilizing group, such as each R$^2$ is —(CH$_2$)x(OCH$_2$CH$_2$)yOCH$_3$ where each x is independently 0 or an integer from 1-20, each y is independently 0 or an integer from 1 to 50; L$^1$ is a fluorene co-monomer of formula (XV) where R$^3$ is an alkyl or an aralkyl substituted with a water solubilizing group (e.g., a PEG substituted alkyl or aralkyl), and R$^4$ is L$^2$-Z$^2$ wherein L$^2$ is a linker and Z$^2$ is a chemoselective tag (e.g., an amino group, —NH$_2$) or a linked acceptor chromophore; at least one of G$^1$ and G$^2$ is a substituted aryl group, e.g., an aryl group substituted with a linker (e.g., a C1-C6 alkyl linker) terminated with a carboxylic acid functional group or a linked specific binding member (e.g., as described herein).

Polymeric Dye Conjugates

In some embodiments of the method, the polymeric dye is a polymeric dye conjugate including a specific binding member that specifically binds a target analyte. Any convenient polymeric dye conjugates may find use in the subject methods. A polymeric dye conjugate includes a specific binding member that is labeled with a polymeric dye (e.g., as described herein). By labeled is meant that the specific binding member and the polymeric dye are linked, directly or indirectly, covalently or non-covalently. In some instances, the polymeric dye conjugate is covalently linked to the specific binding member via an optional linker (e.g., as described herein). A variety of methods of labeling a specific binding member with a polymeric dye may be utilized to fluorescently label the specific binding member, see e.g., the materials and methods described by Greg T. Hermanson in Bioconjugate Techniques, Academic Press, 2$^{nd}$ Ed., 2008. In some cases, labeling involves chemically conjugating a reactive functional group of a polymeric dye, or derivative thereof, to a compatible functional group of a specific binding member, or a derivative thereof. In some instances, the specific binding member is proteinaceous, and labeling involves conjugating the polymeric dye to an amino acid residue of the proteinaceous binding member, e.g., via reaction of an amine functional group with an activated ester (e.g., a N-hydroxysuccinimide active ester). In some embodiments, the polymeric dye is a polymeric tandem dye.

Specific Binding Members

A specific binding member may specifically bind to any convenient target. As used herein, the term "specific binding member" refers to one member of a pair of molecules which have binding specificity for one another. One member of the pair of molecules may have an area on its surface, or a cavity, which specifically binds to an area on the surface of, or a cavity in, the other member of the pair of molecules.

Thus the members of the pair have the property of binding specifically to each other. In some embodiments, the affinity between specific binding members in a binding complex is characterized by a $K_d$ (dissociation constant) of $10^{-6}$ M or less, such as $10^{-7}$ M or less, including $10^{-8}$ M or less, e.g., $10^{-9}$ M or less, $10^{-10}$ M or less, $10^{-11}$ M or less, $10^{-12}$ M or less, $10^{-13}$ M or less, $10^{-14}$ M or less, including $10^{-15}$ M or less. In some embodiments, the proteinaceous specific binding member specifically binds a target of interest with high avidity. By high avidity is meant that the binding member specifically binds with an apparent affinity characterized by an apparent $K_d$ of $10 \times 10^{-9}$ M or less, such as $1 \times 10^{-9}$ M or less, $3 \times 10^{-10}$ M or less, $1 \times 10^{-10}$ M or less, $3 \times 10^{-11}$ M or less, $1 \times 10^{-11}$ M or less, $3 \times 10^{-12}$ M or less or $1 \times 10^{-12}$ M or less.

In some embodiments, the specific binding member is proteinaceous. As used herein, the term "proteinaceous" refers to a moiety that is composed of amino acid residues. A proteinaceous moiety may be a polypeptide. In some embodiments, the proteinaceous specific binding member is an antibody. The antibody molecule may be a whole antibody or an antibody fragment, e.g., a binding fragment of an antibody that specific binds to a polymeric dye. As used herein, the terms "antibody" and "antibody molecule" are used interchangeably and refer to a protein consisting of one or more polypeptides substantially encoded by all or part of the recognized immunoglobulin genes. The recognized immunoglobulin genes, for example in humans, include the kappa (k), lambda (l), and heavy chain genetic loci, which together include the myriad variable region genes, and the constant region genes mu (u), delta (d), gamma (g), sigma (e), and alpha (a) which encode the IgM, IgD, IgG, IgE, and IgA isotypes respectively. An immunoglobulin light or heavy chain variable region consists of a "framework" region (FR) interrupted by three hypervariable regions, also called "complementarity determining regions" or "CDRs". The extent of the framework region and CDRs have been precisely defined (see, "Sequences of Proteins of Immunological Interest," E. Kabat et al., U.S. Department of Health and Human Services, (1991)). The numbering of all antibody amino acid sequences discussed herein conforms to the Kabat system. The sequences of the framework regions of different light or heavy chains are relatively conserved within a species. The framework region of an antibody, that is the combined framework regions of the constituent light and heavy chains, serves to position and align the CDRs. The CDRs are primarily responsible for binding to an epitope of an antigen.

The term antibody is meant to include full length antibodies and may refer to a natural antibody from any organism, an engineered antibody, or an antibody generated recombinantly for experimental, therapeutic, or other purposes as further defined below. Antibodies may be monoclonal or polyclonal and may have other specific activities on cells (e.g., antagonists, agonists, neutralizing, inhibitory, or stimulatory antibodies). It is understood that the antibodies may have additional conservative amino acid substitutions which have substantially no effect on antigen binding or other antibody functions. In certain instances of the method, the specific binding member is an antibody fragment or binding derivative thereof. Antibody fragments of interest include, but are not limited to, Fab, Fab', F(ab')2, Fv, scFv, or other antigen-binding subsequences of antibodies, either produced by the modification of whole antibodies or those synthesized de novo using recombinant DNA technologies.

In certain embodiments, the specific binding member is an antibody fragment or binding derivative thereof selected from an antibody, a Fab fragment, a F(ab')$_2$ fragment, a scFv, a diabody and a triabody. In some cases, the specific binding member is a murine antibody or binding fragment thereof. In certain instances, the specific binding member is a recombinant antibody or binding fragment thereof.

In some cases, a specific binding member can specifically bind a molecule expressed on the surface of a target cell of interest. In certain instances, a specific binding member is a ligand to a target cell receptor. Thus, it can have specific binding affinity for molecules such as T cell surface molecules (e.g., CD3 polypeptides, CD4, CD8, CD2, CD7, cytokine or growth factor receptors, or TCR), B cell surface molecules (e.g., CD19, CD20, CD22, cytokine or growth factor receptors, or Ig molecules), molecules expressed on tumor cells, and molecules expressed on the surface of infected target cells (e.g., viral proteins and glycoproteins). I some cases, the specific binding member may be an antibody, or a binding fragment thereof, against a tumor associated antigen, e.g. the carcinoembryonic antigen. For example, carcinoembryonic antigen (CEA) is a tumor marker which can be present on the membrane cells surface of various cancer such as pancreatic, gastric, colonic, ovarian and breast carcinoma. Other tumor associated antigens of interest are, among others, oncofetal antigens, MART-1, Mage-1, Mage-3, gp 100, tyrosinase, CEA, her2/neu, PSA, CA-125, erb-2, Muc-1, Muc-2, point mutated ras oncogenes, point mutated p53 oncogenes, and TAG-72.

In some cases, the specific binding member is a lectin. In some cases, the specific binding member is a cell adhesion molecule. Exemplary adhesion molecules, that facilitate binding of the polymeric dye conjugate to the cell of interest include, but are not limited to lectin (e.g., wheat germ agglutinin), polycations (e.g., chitosan, polylysine, and the like), laminin, fibrin, fibronectin, integrin, vitronectin, hyaluronic acid, elastin, vitronectin, proteoglycans, glycoproteins, glycosaminoglycans, collagen, gelatin, and the like. The cell adhesion molecule may be attached covalently to the polymeric dye.

In certain instances, the specific binding member is a nucleic acid. In certain instances, the specific binding member is a DNA. In certain instances, the specific binding member is a RNA. The terms "nucleic acid," "nucleic acid molecule", "oligonucleotide" and "polynucleotide" are used interchangeably and refer to a polymeric form of nucleotides of any length, either deoxyribonucleotides or ribonucleotides, or compounds produced synthetically which can hybridize with naturally occurring nucleic acids in a sequence specific manner similar to that of two naturally occurring nucleic acids, e.g., can participate in Watson-Crick base pairing interactions. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, cDNA, recombinant polynucleotides, plasmids, vectors, isolated DNA of any sequence, control regions, isolated RNA of any sequence, nucleic acid probes, primers and any convenient synthetic nucleic acid sequence. The term "polynucleotide" is also meant to encompass nucleic acid analogs, and mixtures of analogs and naturally occurring nucleic acids. Any kind of nucleic acid, such as DNA and RNA, capable of sequence specific hybridization through formation of base pairs—or similar interactions between two moieties—may be utilized to implement the methods described herein, including artificial and unnatural nucleic acid analogs such as PNA, LNA, MNA, ANA, TNA, CeNA, GNA, XNA, HNA, INA, BNA and bicyclo-DNA. Sequence specific pairing of polynucleotides of interest that find use in the subject methods and polymeric dye conjugates may involve natural Watson-Crick base pairing, Hoogsteen pairing, metal ion pairing, or other configurations or pairings between base moieties forming hydrogen bonds, metal ion interactions, or other types of moieties forming sequence specific pairing interactions such as unnatural base pairs (UBP) that may involve hydrogen bonds, hydrophobic interactions or other types of non-covalent bonds.

Specific pairing interactions of polynucleotides may involve natural, unnatural, artificial or modified bases. Analogs or moieties of interest include, but are not limited to, adenine, guanine, thymidine, cytosine, uridine, inosine, thiouridine, 5-bromouracil, methylated bases, 5-methylcytocine and 5-hydroxymethylcytocine, diaminopurine, diaminopyridine, isoguanine, isocytosine, 2'-deoxyinosine, 2-aminoadenine, xanthine, beta-d-glucopyranosyloxymethyluracil, d5SICS, dNaM, 2-amino-8-(2-thienyl)purine, pyridine-2-one, 7-(2-thienyl)imidazo[4,5-b]pyridine, pyrrole-2-carbaldehyde, 4-[3-(6-aminohexanamido)-1-propynyl]-2-nitropyrrole, 2,4-difluorotoluene, 4-methylbenzimidazole, isoquinoline, pyrrolo[2,3-b]pyridine, 2,6-bis(ethylthiomethyl)pyridine, pyridine-2,6-dicarboxamide, and mondentate pyridine. Nucleic acid analogs of interest may include any convenient combination of backbones, bases (or analogs thereof), and pairing moieties that result in a molecule capable of sequence specific binding with a complementary nucleic acid analog of the same or different type which contains a complementary sequence in at least a portion of its sequence.

Specific binding members which specifically bind any convenient target molecules may be selected. Any convenient specific binding members may be utilized. In some embodiments, the specific binding member specifically binds a target selected from the group consisting of, CD11b, CD123, CD14, CD15, CD16, CD19, CD193, CD2, CD25, CD27, CD3, CD335, CD36, CD4, CD43, CD45RO, CD56, CD61, CD7, CD8, CD34, CD1c, CD23, CD304, CD235a, T cell receptor alpha/beta, T cell receptor gamma/delta, CD253, CD95, CD20, CD105, CD117, CD120b, Notch4, Lgr5 (N-Terminal), SSEA-3, TRA-1-60 Antigen, Disialoganglioside GD2 and CD71.

In some embodiments, the specific binding member specifically binds a target cell of interest. In certain embodiments of the method, the target analyte is a cellular target analyte, such as a subcellular target analyte. Specific binding members of interest include, but are not limited to, those affinity agents that specifically bind cell surface proteins of a variety of cell types, including but not limited to, stem cells, T cells, dendritic cells, B Cells, granulocytes, leukemia cells, lymphoma cells, NK cells, macrophages, monocytes, fibroblasts, epithelial cells, endothelial cells and erythroid cells. In certain instances, the specific binding member may be targeted to a subcellular component of the cell, including, but not limited to, extracellular space, cytoplasm, nucleus, mitochondria, Golgi apparatus, endoplasmic reticulum (ER), peroxisome, vacuoles, cytoskeleton, nucleoplasm, nucleolus, nuclear matrix and ribosomes.

In some embodiment, the method further includes contacting the sample with a polymeric dye conjugate that specifically binds the cellular target analyte thereby localizing the polymeric dye conjugate to the cellular target analyte.

Systems

Aspects of the present disclosure include systems for imaging a sample of interest. The system may include a high resolution light microscope and a sample including a polymeric dye that is disposed in a sample field of view. The high resolution light microscope may include: a light source configured to irradiate a sample field of view with an excitation light for a fluorescent polymeric dye; a photodetector configured to detect an emission signal from the sample field of view; and a polarization modulator disposed in the light pathway between the light source and the photodetector. Any convenient microscopes and optical devices may be adapted for use with the subject systems and methods, including but not limited to those microscopes and devices described by Walla et al., Nature Methods 11, 579-584 (2014); and Canadian Patent Application 2858270, the disclosure of which is herein incorporated by reference.

The systems may include a light source capable of irradiating the sample interrogation field of view with excitation light for a polymeric dye of interest. In some embodiments, the light source is a broadband light source, emitting light having a broad range of wavelengths, such as for example, spanning 50 nm or more, such as 100 nm or more, such as 150 nm or more, such as 200 nm or more, such as 250 nm or more, such as 300 nm or more, such as 350 nm or more, such as 400 nm or more and including spanning 500 nm or more. For example, one suitable broadband light source emits light having wavelengths from 200 nm to 1500 nm, such as from 300 nm to 400 nm. Another example of a suitable broadband light source includes a light source that emits light having wavelengths from 400 nm to 1000 nm. Any convenient broadband light source protocol may be employed, such as a halogen lamp, deuterium arc lamp, xenon arc lamp, stabilized fiber-coupled broadband light source, a broadband LED with continuous spectrum, superluminescent emitting diode, semiconductor light emitting diode, wide spectrum LED white light source, an multi-LED integrated white light source, among other broadband light sources or any combination thereof.

In other embodiments, the light source is a narrow band light source emitting a particular wavelength or a narrow range of wavelengths. In some instances, the narrow band light sources emit light having a narrow range of wavelengths, such as for example, 50 nm or less, such as 40 nm or less, such as 30 nm or less, such as 25 nm or less, such as 20 nm or less, such as 15 nm or less, such as 10 nm or less, such as 5 nm or less, such as 2 nm or less and including light sources which emit a specific wavelength of light (i.e., monochromatic light). Any convenient narrow band light source protocol may be employed, such as a narrow wavelength LED, laser diode or a broadband light source coupled to one or more optical bandpass filters, diffraction gratings, monochromators or any combination thereof.

Light sources of interest include, but are not limited to, lasers, photodiodes, and lamps, including mercury or xenon lamps, a flash lamp, incandescent bulb or any other light source suitable for excitation of fluorescence. In certain embodiments, the light source is a laser. In some instances, the subject systems include a gas laser, such as a helium-neon laser, argon laser, krypton laser, xenon laser, nitrogen laser, $CO_2$ laser, CO laser, argon-fluorine (ArF) excimer laser, krypton-fluorine (KrF) excimer laser, xenon chlorine (XeCl) excimer laser or xenon-fluorine (XeF) excimer laser or a combination thereof. In others instances, the subject systems include a dye laser, such as a stilbene, coumarin or rhodamine laser. In yet other instances, lasers of interest include a metal-vapor laser, such as a helium-cadmium (HeCd) laser, helium-mercury (HeHg) laser, helium-selenium (HeSe) laser, helium-silver (HeAg) laser, strontium laser, neon-copper (NeCu) laser, copper laser or gold laser and combinations thereof. In still other instances, the subject systems include a solid-state laser, such as a ruby laser, an Nd:YAG laser, NdCrYAG laser, Er:YAG laser, Nd:YLF laser, Nd:YVO$_4$ laser, Nd:YCa$_4$O(BO$_3$)$_3$ laser, Nd:YCOB laser, titanium sapphire laser, thulim YAG laser, ytterbium YAG laser, ytterbium$_2$O$_3$ laser or cerium doped lasers and combinations thereof.

The subject systems may include one or more light sources, as desired, such as two or more light sources, such as three or more light sources, such as four or more light sources, such as five or more light sources and including ten or more light sources. The light source may include any combination of types of light sources. For example, in some embodiments, the subject systems include an array of lasers, such as an array having one or more gas lasers, one or more dye lasers and one or more solid-state lasers. In other instances, where two lights sources are employed, a first light source may be a broadband white light source (e.g., broadband white light LED) and second light source may be a broadband near-infrared light source (e.g., broadband near-IR LED). In other instances, where two light sources are employed, a first light source may be a broadband white light source (e.g., broadband white light LED) and the second light source may be a narrow spectra light source (e.g., near-IR LED or laser). In yet other instances, the light source is a plurality of narrow band light sources each emitting specific wavelengths, such as two or more lasers, such as three or more lasers including 5 or more lasers. In still other instances, the light source is an array of two or more LEDs, such as an array of three or more LEDs, such as an array of five or more LEDs, including an array of ten or more LEDs.

In some embodiments, light sources emit light having wavelengths ranging from 200 nm to 1500 nm, such as from 250 nm to 1250 nm, such as from 300 nm to 1000 nm, such as from 350 nm to 900 nm and including from 400 nm to 800 nm. For example, the light source may include a broadband light source emitting light having wavelengths from 200 nm to 900 nm. In other instances, the light source includes a plurality of narrow band light sources emitting wavelengths ranging from 200 nm to 900 nm. For example, the light source may be plurality of narrow band LEDs (1 nm-25 nm) each independently emitting light having a range of wavelengths between 200 nm to 900 nm. In some embodiments, the narrow band light source is one or more narrow band lamps emitting light in the range of 200 nm to 900 nm, such as a narrow band cadmium lamp, cesium lamp, helium lamp, mercury lamp, mercury-cadmium lamp, potassium lamp, sodium lamp, neon lamp, zinc lamp or any combination thereof. In other embodiments, the narrow band light source includes one or more lasers emitting light in the range of 200 nm to 1000 nm, such as gas lasers, excimer lasers, dye lasers, metal vapor lasers and solid-state laser as described above.

In some instances of the system, the light source is a source of polarized excitation light. Light may be polarized using a polarization modulator (i.e., polarizer), such as a polarization filter which passes light of a particular desired polarization and blocks waves of other polarizations. In some embodiments of the system, the polarization modulator is configured to modulate the polarization angle of polarized excitation light from a first polarization angle to a second polarization angle. Any convenient devices and optical elements may find use as a polarization modulator in the subject systems. Polarization modulators of interest include, but are not limited to, electro-optical modulators, magneto-optical modulators and photoelastic modulators. Polarization devices of interest which find use in the subject systems include, but are not limited to, those described by Bass M (1995) Handbook of Optics, Second edition, Vol. 2, Ch. 22.19, McGraw-Hill, ISBN 0-07-047974-7. In some instances, the polarization modulator is a polarization rotator. A polarization rotator is an optical device that is capable of rotating the polarization axis of a linearly polarized beam of light by a polarization angle of choice. The beam of light may be in the excitation pathway (i.e., an excitation light) or in the emission pathway (e.g., emission signal) of the system. The polarization rotators may be configured to operate on a principle of birefringence or total internal reflection. In some instances, the polarization modulator is located in the excitation pathway of the system (i.e., between the light source and the sample field of view).

In certain instances of the system, the excitation light is not polarized. In some embodiments, the system includes a polarization modulator that is configured to restrict the polarization of incident light at the photodetector (e.g., an emission signal originating from a polymeric dye of interest). As such, in some instances, the polarization modulator is located in the emission pathway of the system (i.e., between the sample field of view and the detector). In certain instances of the system, the polarization modulator is configured to modulate the polarization of the incident light at the photodetector from a first polarization angle to a second polarization angle.

Systems of the present disclosure also include one or more detectors. Detectors of interest may include, but are not limited to, optical sensors or photodetectors, such as active-pixel sensors (APSs), avalanche photodiode, image sensors, charge-coupled devices (CODs), intensified charge-coupled devices (ICCDs), light emitting diodes, photon counters, bolometers, pyroelectric detectors, photoresistors, photovoltaic cells, photodiodes, photomultiplier tubes, phototransistors, quantum dot photoconductors or photodiodes and combinations thereof, among other photodetectors. In certain embodiments, the transmitted light is measured with a charge-coupled device (CCD), semiconductor charge-coupled devices (CCD), active pixel sensors (APS), complementary metal-oxide semiconductor (CMOS) image sensors or N-type metal-oxide semiconductor (NMOS) image sensors. In some embodiments, the imaging sensor is a CCD camera. For example, the camera may be an electron multiplying CCD (EMCCD) camera or an intensified CCD (ICCD) camera. In other embodiments, the imaging sensor is a CMOS-type camera. Where the transmitted light is measured with a CCD, the active detecting surface area of the CCD may vary, such as from 0.01 cm$^2$ to 10 cm$^2$, such as from 0.05 cm$^2$ to 9 cm$^2$, such as from, such as from 0.1 cm$^2$ to 8 cm$^2$, such as from 0.5 cm$^2$ to 7 cm$^2$ and including from 1 cm$^2$ to 5 cm$^2$. The number of photodetectors in the subject systems may vary, as desired.

Detectors of interest may be configured to measure light emitted by a sample in the field of view at one or more wavelengths, such as at 2 or more wavelengths, such as at 5 or more different wavelengths, such as at 10 or more different wavelengths, such as at 25 or more different wavelengths, such as at 50 or more different wavelengths, such as at 100 or more wavelengths, such as at 200 or more different wavelengths, such as at 300 or more different wavelengths and including measuring light emitted by a sample in the field of view at 400 or more different wavelengths.

In some embodiments, detectors of interest are configured to measure light emitted by a sample in the field of view over a range of wavelengths (e.g., 200 nm-1000 nm). In certain embodiments, detectors of interest are configured to collect spectra of light over a range of wavelengths. For example, systems may include one or more detectors configured to collect spectra of light over one or more of the wavelength ranges of 200 nm-1000 nm. In certain embodiments, detectors of interest are configured to measure light emitted by a sample in the field of view at one or more specific wavelengths. For example, systems may include one or more detectors configured to measure light at one or more of 450 nm, 518 nm, 519 nm, 561 nm, 578 nm, 605 nm, 607 nm, 625 nm, 650 nm, 660 nm, 667 nm, 670 nm, 668 nm, 695 nm, 710 nm, 723 nm, 780 nm, 785 nm, 647 nm, 617 nm and any combinations thereof. In certain embodiments, one or more detectors may be configured to be paired with specific polymeric dyes of interest, such as those used with the sample in a fluorescence assay.

In embodiments, the detector is configured to measure light continuously or in discrete intervals. In some instances, detectors of interest are configured to take measurements of the light emitted by a sample in the field of view continuously. In other instances, detectors of interest are configured to take measurements in discrete intervals, such as measuring light every 0.001 millisecond, every 0.01 millisecond, every 0.1 millisecond, every 1 millisecond, every 10 milliseconds, every 100 milliseconds and including every 1000 milliseconds, or some other interval. The detector may be configured to measure light in conjunction with the operation of the polarization modulator. For example, the detector may be configured to capture an image of the sample field of view corresponding to a particular polarization angle configuration of the polarization modulator.

Wavelength separators refer to an optical protocol for separating polychromatic light into its component wavelengths for detection. Wavelength separation, according to certain embodiments, may include selectively passing or blocking specific wavelengths or wavelength ranges of the polychromatic light. To separate wavelengths of light, the light emitted by a sample in the field of view may be passed through any convenient wavelength separating protocol, including but not limited to colored glass, bandpass filters, interference filters, dichroic mirrors, diffraction gratings, monochromators and combinations thereof, among other wavelength separating protocols.

In some embodiments, detectors include one or more optical filters, such as one or more bandpass filters. For example, optical filters of interest may include bandpass filters having minimum bandwidths ranging from 2 nm to 100 nm, such as from 3 nm to 95 nm, such as from 5 nm to 95 nm, such as from 10 nm to 90 nm, such as from 12 nm to 85 nm, such as from 15 nm to 80 nm and including bandpass filters having minimum bandwidths ranging from 20 nm to 50 nm. In some embodiments, the wavelength separator is a diffraction grating. Diffraction gratings may include, but are not limited to transmission, dispersive or reflective diffraction gratings. Suitable spacings of the diffraction grating may vary depending on the configuration of the flow nozzle chamber, detector and other optical adjust protocols present (e.g., focusing lens), ranging from 0.01 µm to 10 µm, such as from 0.025 µm to 7.5 µm, such as from 0.5 µm to 5 µm, such as from 0.75 µm to 4 µm, such as from 1 µm to 3.5 µm and including from 1.5 µm to 3.5 µm.

In certain embodiments, the system further includes a processor operably coupled to a memory that includes instructions stored thereon to: modulate the polarization of the emission signals through a first range of polarization angles; and to simultaneously collect images of the emission signal from the photoluminescent polymeric dye in the sample field of view that correspond to the polarization angles. A "processor" references any hardware and/or software combination that will perform the functions required of it. For example, any processor herein may be a programmable digital microprocessor such as available in the form of an electronic controller, mainframe, server or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station.

In some embodiments, the processor is configured to operate the high resolution light microscope in a manner so that it operates to collect images of the sample field of view at a variety of polarization angles (e.g., of excitation light or emission signal), by having an appropriate control algorithm recorded onto a processor or control element of the device. The images may be recorded and integrated to build a high-resolution fluorescent image of the sample field of view. In certain embodiments, the system is configured for sub diffraction-limited imaging of the sample in the sample field of view. In some instances, the system is configured for super-resolution imaging of the sample in the sample field of view. The system may be configured to provide super-resolution imaging of a sample of interest at a resolution of 500 nm or less, such as 300 nm or less, 250 nm or less, 200 nm or less, 150 nm or less, 100 nm or less, 90 nm or less, 80 nm or less, 70 nm or less, 60 nm or less, 50 nm or less, 40 nm or less, 30 nm or less, 20 nm or less, 10 nm or less, or even less.

The system may include a sample (e.g., as described herein) disposed in the field of view, where the sample include a polymeric dye of interest (e.g., as described herein). In some embodiments of the system, the polymeric dye is a polymeric tandem dye. In certain embodiments of the system, the polymeric dye is a polymeric dye conjugate including a specific binding member. In certain instances of the system, the sample is a cellular sample. In some instances of the system, the polymeric dye is spatially distributed at a plurality of locations in the sample. In some cases, the system is configured to image, at discrete polarization angles, discrete subsets of the polymeric dye molecules at the plurality of locations in the sample.

Utility

The subject methods and systems as described herein find use in a variety of applications, such as diagnostic and research applications where it is desirable to image a sample that has been labeled with a fluorescent dye. Applications of interest include the super-resolution imaging of cells to probe particular cellular functions such as signal transduction and gene expression. In some cases, the subject methods and systems find use in the super-resolution imaging of fixed permeabilized cells, e.g., in the detection and investigation of intracellular antigens using antibody probes. In certain instances, the subject methods and systems find use in the multicolor super-resolution imaging of cell-surface proteins in live cells, e.g., to detect and investigate co-localization of proteins in response to signaling events. The subject methods and systems may also find use in the multicolor super-resolution imaging of a variety of biological processes of interest such as embryogenesis, organogenesis and formation of cell-cell contacts.

The following examples are offered by way of illustration and not by way of limitation.

EXPERIMENTAL

Example 1: High Brightness, Water-Solubility and Strong Polarization-Dependent Excitation of Sirigen Dyes Povide Super Resolution and Contrast in Multicolor Fluorescence Imaging Polymeric dyes confer substantially improved brightness compared to small molecule dyes in polarization-modulated fluorescence microscopy and thus improve spatial resolution. The resolution of super-resolution fluorescence microscopy by excitation polarization modulation (SPoD) imaging of small molecules can be improved using a secondary illumination source, of polarization perpendicular to that of the excitation source, which serves to limit the number of fluorophores which are excited at a given polarization angle (i.e. excitation polarization angle narrowing, Ex PAN). By reducing the number of fluorophores excited, the spatial resolution of overlapping molecules can be improved. The stronger polarization-dependence of polymeric dyes (e.g., Sirigen dyes) obviate the need for this secondary illumination source, without compromising resolvability of closely spaced dyes and thus further simplifies the optical set-up required to achieve super-resolution imaging. The water-soluble nature of Sirigen polymeric dyes and ability to chemically link them to specific affinity agents (e.g. antibodies) provides photoluminescent conjugated polymers suitable for SPoD imaging. Polymeric dyes can be tailored to emit light at a wide range of wavelengths, provideing a readily-accessible route to multicolor super-resolution imaging.

Sub-diffraction-limited fluorescence microscopy includes stochastic optical reconstruction microscopy (STORM), photoactivated localization microscopy (PALM), stimulated emission depletion microscopy (STED) and structured illumination microscopy (SIM). STORM/PALM-based techniques rely upon random switching of fluorophores between fluorescent and non-fluorescent states to localize the positions of individual fluorescent molecules. This photoswitching behavior is mediated by costly high power lasers, special buffer compositions and restricted to dyes which exhibit adequate rates of switching between dark and emissive states. Use of polymeric dyes in super-resolution microscopy by means of modulated excitation/emission polarization avoids the use of additional high-power lasers to mediate photoswitching behavior, is independent of buffer compositions, utilizes relatively low cost polarizing filters and enables substantially reduced image acquisition times. STED and SIM-based techniques are critically-dependent on the use of high precision optics, multiply aligned lasers, time-consuming laser scanning of specimens and sophisticated filters to attain super resolution imaging. Polymeric dyes in conjunction with modulated excitation polarization imaging substantially reduces the complexity of optical apparatus required relative to STED/SIM.

Example 2

FIG. 1 shows a series of panels illustrating a method of imaging a sample of interest: Panel 1: Polymeric dyes in a sample assume random orientations; Panel 2: A subset of the polymeric dyes are excited with plane polarized light and fluorescence is detected. Only those polymeric dyes with transition dipole moments oriented parallel to the direction of polarization are excited; Panel 3: Coordinates of polymeric dyes are determined by tilting the point spread function to a 2-dimensional Gaussian function. The Gaussian function is used as a simple and easy to implement Point Spread Function (PSF) model for fitting the position of fluorescent emitters in localization microscopy. The high number of photons delivered to the detector from polymeric dyes of interest provides a high accuracy of localization; Panel 4: The polarization angle is modulated allowing another subset of polymeric dyes of different orientation to become emissive. The coordinates are subsequently determined as in step 3; Panel 5: Modulating across several of polarization angles allows spatial coordinates of all fluorophores within the sample to be recorded to high accuracy; and Panel 6: Imaging with non-polarized light obfuscates resolution of closely-spaced fluorophores.

Notwithstanding the appended claims, the disclosure set forth herein is also defined by the following clauses:

1. A method for producing a high resolution image of a sample, the method comprising: (a) detecting first and second sets of spatially-dependent emission signals from a sample labeled with a fluorescent polymeric dye; and (b) producing a high resolution fluorescence image of the sample from the detected first and second sets of spatially-dependent emission signals.

2. The method according to Clause 1, wherein step (a) comprises irradiating the sample with polarized excitation light to produce the first and second spatially-dependent emission signals.

3. The method according to Clause 2, wherein step (a) comprises modulating the polarization angle of the polarized excitation light from a first polarization angle at which the first set of spatially-dependent emission signals is produced to a second polarization angle at which the second set of spatially-dependent emission signals is produced.

4. The method according to Clause 3, wherein the polymeric dye located at a first location in the sample has a first emission signal at the first polarization angle and a second emission signal at the second polarization angle.

5. The method according to any one of Clauses 2-4, wherein the polymeric dye is spatially distributed at a plurality of locations in the sample and emits emission signals from the plurality of locations that are each dependent on the polarization angle of the polarized excitation light.

6. The method according to Clause 1, wherein emission light from the sample is polarized to produce the first and second spatially-dependent emission signals.

7. The method according to Clause 6, wherein step (a) comprises irradiating the sample with unpolarized excitation light.

8. The method according to any one of Clauses 6 and 7, wherein step (a) comprises modulating the polarization angle of the emission light from a first polarization angle at which the first set of spatially-dependent emission signals is produced to a second polarization angle at which the second set of spatially-dependent emission signals is produced.

9. The method according to any one of Clauses 6-8, wherein the polymeric dye located at a first location in the sample has a first emission signal at the first polarization angle and a second emission signal at the second polarization angle.

10. The method according to any one of Clauses 4 and 9, wherein the difference between the first emission signal and the second emission signal corresponds to an intensity for the first location in the high resolution fluorescence image.
11. The method according to any one of Clauses 2 and 7, wherein the irradiating is continuous.
12. The method according to any one of Clauses 2 and 7, wherein the irradiating is pulsed.
13. The method according to any one of Clauses 2, 7 and 11-12, wherein the irradiating comprises simultaneously irradiating the entire sample.
14. The method according to any one of Clauses 2 and 7, wherein the excitation light source is a laser.
15. The method according to any one of Clauses 2 and 7, wherein the excitation light source is a coherent light source.
16. The method according to any one of Clauses 1-15, wherein the polymeric dye has an absorption maximum wavelength in the ultraviolet region.
17. The method according to any one of Clauses 1-15, wherein the polymeric dye has an absorption maximum wavelength in the visible region.
18. The method according to any one of Clauses 6-9, wherein the polarized emission light is linearly polarized.
19. The method according to any one of Clauses 3 and 8, wherein the modulating comprises modulating the linear polarization angle of the polarized excitation light in the range from 0 to 180°.
20. The method according to any one of Clauses 1-19, wherein the sample is a biological sample.
21. The method according to any one of Clauses 1-20, wherein the sample is a cellular sample.
22. The method according to any one of Clauses 1-21, wherein the sample is a cell.
23. The method according to any one of Clauses 1-21, wherein the high resolution fluorescence image is a sub diffraction-limited image of the sample.
24. The method according to any one of Clauses 1-23, further comprising repeating the steps of the method one or more times to produce a time lapse image of the sample.
25. The method according to any one of Clauses 1-24, wherein the fluorescent polymeric dye comprises a conjugated polymer.
26. The method according to Clause 25, wherein the conjugated polymer comprises a rigid-rod structure.
27. The method according to any one of Clauses 1-26, wherein the polymeric dye is a polymeric tandem dye comprising an acceptor chromophore.
28. The method according to Clause 27, wherein the acceptor chromophore is a fluorophore.
29. The method according to any one of Clauses 1-28, wherein the polymeric dye is a polymeric dye conjugate comprising a specific binding member that specifically binds a target analyte.
30. The method according to Clause 29, wherein the specific binding member is an antibody.
31. The method according to Clause 29, wherein the specific binding member is an antibody fragment or binding derivative thereof.
32. The method according to Clause 31, wherein the antibody fragment or binding derivative thereof is selected from the group consisting of a Fab fragment, a F(ab')$_2$ fragment, a scFv, a diabody and a triabody.
33. The method according to Clause 29, wherein the specific binding member is a lectin.
34. The method according to Clause 29, wherein the specific binding member is a nucleic acid.
35. The method according to any one of Clauses 29-34, wherein the target analyte is a cellular target analyte.
36. The method according to Clause 35, further comprising contacting the sample with a polymeric dye conjugate that specifically binds the cellular target analyte thereby localizing the polymeric dye conjugate to the location of the cellular target analyte.
37. The method according to any one of Clauses 1-36, wherein the sample comprises a first polymeric dye having a first emission maximum wavelength and a second polymeric dye having a second emission maximum wavelength and the step (a) comprises detecting first and second sets of spatially-dependent emission signals from the sample at first and second emission maximum wavelengths.
38. A method for high resolution imaging of a cell, the method comprising:
(a) contacting a cell labeled with a polymeric dye conjugate that specifically binds a subcellular target under conditions in which the polymeric dye conjugate is localized to the subcellular target location; (b) detecting first and second sets of spatially-dependent emission signals from the sample; and (c) producing a high resolution fluorescence image of the cell from the detected first and second sets of spatially-dependent emission signals.
39. The method according to Clause 38, wherein step (b) comprises irradiating the cell with polarized excitation light to produce the first and second spatially-dependent emission signals.
40. The method according to Clause 39, wherein step (b) comprises modulating the polarization angle of the polarized excitation light from a first polarization angle at which the first set of spatially-dependent emission signals is produced to a second polarization angle at which the second set of spatially-dependent emission signals is produced.
41. The method according to Clause 40, wherein the polymeric dye located at the subcellular target location in the cell and has a first emission signal at the first polarization angle and a second emission signal at the second polarization angle.
42. The method according to Clause 38, wherein emission light from the cell is polarized to produce the first and second spatially-dependent emission signals.
43. The method according to Clause 38, wherein step (b) comprises irradiating the sample with unpolarized excitation light.
44. The method according to Clause 43, wherein step (b) comprises modulating the polarization angle of the emission light from a first polarization angle at which the first set of spatially-dependent emission signals is produced to a second polarization angle at which the second set of spatially-dependent emission signals is produced.
45. The method according to Clause 44, wherein the polymeric dye located at the subcellular target location has a first polarized emission signal at the first polarization angle and a second polarized emission signal at the second polarization angle.
46. The method according to any one of Clauses 44 and 45, wherein the difference between the first emission signal and the second emission signal corresponds to an intensity for the subcellular target location in the high resolution fluorescence image.
47. The method according to any one of Clauses 38-46, further comprising contacting the cell with a second polymeric dye conjugate that specifically binds a second subcellular target and has a second emission wavelength maximum.
48. The method according to any one of Clauses 38-47, further comprising determining the spatial location of the subcellular target location in the cell.
49. A system for imaging a sample, the system comprising:
   a high resolution light microscope comprising:
      a light source configured to irradiate a sample field of view with an excitation light for a fluorescent polymeric dye;
      a photodetector configured to detect an emission signal from the sample field of view: and
      a polarization modulator disposed in the light pathway between the light source and the photodetector; and
   a sample labeled with a polymeric dye and disposed in the sample field of view.
50. The system according to Clause 49, wherein the polarization modulator is disposed in the light pathway between the light source and the sample and is configured to polarize the excitation light.
51. The system according to Clause 50, wherein the polarization modulator is configured to modulate the polarization angle of polarized excitation light from a first polarization angle to a second polarization angle.
52. The system according to Clause 49, wherein the polarization modulator is disposed in the light pathway between the sample and the photodetector and configured to polarize incident light at the photodetector.
53. The system according to Clause 52, wherein the excitation light is unpolarized.
54. The system according to Clause 53, wherein the polarization modulator is configured to modulate the polarization of the incident light at the photodetector from a first polarization angle to a second polarization angle.
55. The system according to any one of Clauses 49-54, wherein the polymeric dye is spatially distributed at a plurality of locations in the sample.
56. The system according to Clause 49, further comprising a processor operably coupled to a memory that includes instructions stored thereon to: modulate the polarization angle of the polarization modulator through a plurality of polarization angles; simultaneously detect a plurality of sets of emission signals from the sample field of view; and produce a high resolution fluorescence image of the sample field of view from the detected plurality of sets of emission signals.
57. The system according to any one of Clauses 49-56, wherein the system is configured for sub diffraction-limited imaging of the sample in the sample field of view.
58. The system according to any one of Clauses 49-57, wherein the polymeric dye is a polymeric dye conjugate comprising a specific binding member.
59. The system according to any one of Clauses 49-58, wherein the polymeric dye is a polymeric tandem dye.
60. The system according to any one of Clauses 49-59, wherein the sample is a cellular sample.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the following.

What is claimed is:

1. A method for producing a high resolution image of a sample, the method comprising:
   (a) irradiating a sample labeled with a fluorescent polymeric dye comprising a conjugated polymer with a first excitation light and detecting a first set of spatially-dependent emission signals from the sample;
   (b) irradiating the sample with a second excitation light and detecting a second set of spatially-dependent emission signals from the sample; and
   (c) producing a high resolution fluorescence image of the sample by collecting and integrating the detected first and second sets of spatially-dependent emission signals.

2. The method according to claim 1, wherein steps (a) and (b) comprise irradiating the sample with polarized excitation light to produce the first and second spatially-dependent emission signals.

3. The method according to claim 2, wherein steps (a) and (b) comprise modulating the polarization angle of the polarized excitation light from a first polarization angle at which the first set of spatially-dependent emission signals is produced to a second polarization angle at which the second set of spatially-dependent emission signals is produced.

4. The method according to claim 3, wherein the polymeric dye located at a first location in the sample has a first emission signal at the first polarization angle and a second emission signal at the second polarization angle.

5. The method according to claim 4, wherein the difference between the first emission signal and the second emission signal corresponds to an intensity for the first location in the high resolution fluorescence image.

6. The method according to claim 1, wherein emission light from the sample is polarized to produce the first and second spatially-dependent emission signals.

7. The method according to claim 6, wherein steps (a) and (b) comprise modulating the polarization angle of the emission light from a first polarization angle at which the first set of spatially-dependent emission signals is produced to a second polarization angle at which the second set of spatially-dependent emission signals is produced.

8. The method according to claim 1, wherein the high resolution fluorescence image is a sub diffraction-limited image of the sample.

9. The method according to claim 1, wherein the polymeric dye is provided as a polymeric dye conjugate comprising the polymeric dye comprising a conjugated polymer and a specific binding member that specifically binds a target analyte.

10. The method according to claim 9, wherein the target analyte is a cellular target analyte.

11. The method according to claim 1, wherein the conjugated polymer comprises a rigid-rod structure.

12. The method according to claim 1, wherein the sample is a biological sample.

13. The method according to claim 1, wherein the excitation light source is a laser.

14. The method according to claim 1, wherein the polymeric dye has an absorption maximum wavelength in the ultraviolet region.

15. The method according to claim 1, further comprising repeating the steps of the method one or more times to produce a time lapse image of the sample.

16. A method for high resolution imaging of a cell, the method comprising:
   (a) contacting a cell labeled with a fluorescent polymeric dye comprising a conjugated polymer bound to a specific binding member that specifically binds a subcellular target under conditions in which the polymeric dye conjugate is localized to the subcellular target location;
   (b) irradiating the sample with a first excitation light and detecting a first set of spatially-dependent emission signals from the sample;
   (c) irradiating the sample with a second excitation light and detecting a second set of spatially-dependent emission signals from the sample; and
   (d) producing a high resolution fluorescence image of the cell by collecting and integrating the detected first and second sets of spatially-dependent emission signals.

17. The method according to claim 16, wherein steps (b) and (c) comprise irradiating the cell with polarized excitation light to produce the first and second spatially-dependent emission signals; and modulating the polarization angle of the polarized excitation light from a first polarization angle at which the first set of spatially-dependent emission signals is produced to a second polarization angle at which the second set of spatially-dependent emission signals is produced.

18. The method according to claim 16, wherein emission light from the cell is polarized to produce the first and second spatially-dependent emission signals; and
   steps (b) and (c) comprise modulating the polarization angle of the emission light from a first polarization angle at which the first set of spatially-dependent emission signals is produced to a second polarization angle at which the second set of spatially-dependent emission signals is produced.

19. The method according to claim 16, further comprising determining the spatial location of the subcellular target location in the cell.

* * * * *